US012740996B2

(12) United States Patent
Lee et al.

(10) Patent No.: US 12,740,996 B2
(45) Date of Patent: Sep. 22, 2026

(54) CANCER-SPECIFIC TRANS-SPLICING RIBOZYME EXPRESSING IMMUNE CHECKPOINT INHIBITOR, AND USE THEREOF

(71) Applicant: Rznomics Inc., Yongin-si (KR)

(72) Inventors: Seong-Wook Lee, Seoul (KR); Eun Yi Cho, Yongin-si (KR); Tae Young Kim, Incheon (KR); Hye Rim Park, Bucheon-si (KR)

(73) Assignee: Rznomics Inc., Yongin-si (KR)

( * ) Notice: Subject to any disclaimer, the term of this patent is extended or adjusted under 35 U.S.C. 154(b) by 636 days.

(21) Appl. No.: 18/034,533

(22) PCT Filed: Jan. 21, 2022

(86) PCT No.: PCT/KR2022/001088

§ 371 (c)(1),
(2) Date: Apr. 28, 2023

(87) PCT Pub. No.: WO2022/158891

PCT Pub. Date: Jul. 28, 2022

(65) Prior Publication Data

US 2023/0390320 A1 Dec. 7, 2023

(30) Foreign Application Priority Data

Jan. 25, 2021 (KR) ........................ 10-2021-0010416
Dec. 31, 2021 (KR) ........................ 10-2021-0193826

(51) Int. Cl.
*A61K 31/7088* (2006.01)
*A61P 35/00* (2006.01)
*C12N 15/63* (2006.01)

(52) U.S. Cl.
CPC .......... *A61K 31/7088* (2013.01); *A61P 35/00* (2018.01); *C12N 15/63* (2013.01)

(58) Field of Classification Search
CPC .................................................. A61K 31/7088
See application file for complete search history.

(56) References Cited

U.S. PATENT DOCUMENTS

2020/0071401 A1 3/2020 Jarjour et al.
2020/0270612 A1* 8/2020 Lee .................... C12N 15/1137

FOREIGN PATENT DOCUMENTS

JP 2014-524253 A 9/2014
JP 2016-531567 A 10/2016
JP 2017-532032 A 11/2017
JP 2020-146033 A 9/2020
KR 10-1034811 B1 5/2011
KR 10-2013-0020492 A 2/2013
KR 10-1478869 B1 1/2015
KR 10-2015-0021839 A 3/2015
KR 10-2016-0038674 A 4/2016
KR 10-2020-0102943 A 9/2020
WO 2006/042232 A2 4/2006

OTHER PUBLICATIONS

Szymczak et al., "Development of 2A peptide-based strategies in the design of multicistronic vectors", Expert Opin. Biol, Ther., 2005 5(5), pp. 627-638.
Juhyun Kim, et al., "Targeted Regression of Hepatocellular Carcinoma by Cancer-Specific RNA Replacement through MicroRNA Regulation", Scientific Reports, Jul. 20, 2015, vol. 5, No. 12315, DOI:10.1038/srep12315 (14 pages).
Andrea L Szymczak et al., "Correction of Multi-gene deficiency in vivo using a single 'self-cleaving' 2A peptide-based retroviral vector", Nature Biotechnology, May 2004, vol. 22, No. 5, pp. 589-594 and p. 760 (8 pages).
Yuancheng Wang et al., "2A self-cleaving peptide-based multi-gene expression system in the silkworm Bombyx mori", Scientific Reports, Nov. 5, 2015, vol. 5, No. 16273, pp. 1-10 (11 pages).
Seung-Pil Shin, et al., "Adenovirus Expressing Both Thymidine Kinase and Soluble PD1 Enhances Antitumor Immunity by Strengthening CD8 T-cell Response ", Molecular Therapy, Mar. 2013, www.moleculartherapy.org, vol. 21, No. 3,pp. 688-695 (9 pages).
Maria-Carmela Speranza et al., "Preclinical investigation of combined gene-mediated cytotoxic immunotherapy and immune checkpoint blockade in glioblastoma", Neuro-Oncology, 2018, pp. 225-235, 20(2).
International Search Report for PCT/KR2022/001088, dated May 4, 2022.
H.H. Seo et al., "Soluble PD1 enhances anti-immunity in orthotopic bladder tumors by strengthening CD8 T cell response," The European Society for Gene and Cell Therapy and the Spanish Society for Gene and Cell Therapy Collaborative Congress, 2013 Conference, Abstract, Madrid, Spain, Oct. 25-28, 2013, Poster Presentation P385 (5 pgs. total).

* cited by examiner

*Primary Examiner* — Suzanne M Noakes
(74) *Attorney, Agent, or Firm* — Sughrue Mion, PLLC

(57) ABSTRACT

The present disclosure relates to a cancer-specific trans-splicing ribozyme and a use thereof. The trans-splicing ribozyme does not act on normal tissues but is specifically expressed in cancer tissues, and thus the safety thereof is high and the expression efficiency thereof is excellent at the post-transcription level, and one or more target genes are connected to the 3' exon of the ribozyme so that a cancer therapeutic gene and an immune checkpoint inhibitor are expressed together when applied in vivo, and thus the present disclosure can be effectively used in cancer treatment.

15 Claims, 28 Drawing Sheets

Specification includes a Sequence Listing.

All data are represented as mean ± SD.
**, P<0.01; *, P<0.05

```
                       SEQUENCE LISTING

<160> NUMBER OF SEQ ID NOS: 13

<210> SEQ ID NO 1
<211> LENGTH: 744
<212> TYPE: DNA
<213> ORGANISM: Artificial Sequence
<220> FEATURE:
<223> OTHER INFORMATION: gene encoding scFv PD1(I)

<400> SEQUENCE: 1

caggtacaac ttgttcagtc cggagctgaa gtgaaaaagc cgggcgcgtc tgttaaggta     60

agctgcaagg cttcaggcta tactttcacg gcgcagtaca tgcattgggt cagacaagct    120

ccaggccaag gtcttgaatg gatggggatc atcaacccga gtgggggtga aacaggctat    180

gctcaaaagt tccagggtcg agtcaccatg actcgggata cctccacgtc taccgtttac    240

atggagctga gcagtttgag gagcgaagat actgccgtat actattgtgc caaggaaggt    300

gttgcggacg gttatgggct cgttgatgta tgggggcaag gcacgatggt taccgtctca    360

tctggtggag gaggttctgg gggtggaggc tcaggaggag gggggtcagg tggcggagga    420

tccgaaatcg tgttgaccca gagtcctgca acactgagtc tgtccccagg ggagagagcc    480

accttgtcct gtagagcgag ccagtctgta agctcttatc tggcttggta tcagcaaaaa    540

cctgggcagg cgccgcgcct cctcatctat gacgcgagca agagggcaac agggatacca    600

gcgagattct ctgggtcagg atcagggaca gacttcacac tcacgatcag ctctttggaa    660

ccagaagatt ttgcagtcta ctattgtgat caacgaaaca actggcctct cacgttcgga    720

ggagggacta aagtagaaat taaa                                           744


<210> SEQ ID NO 2
<211> LENGTH: 720
<212> TYPE: DNA
<213> ORGANISM: Artificial Sequence
<220> FEATURE:
<223> OTHER INFORMATION: gene encoding scFv PD1(N)

<400> SEQUENCE: 2

caggtccaac ttgtcgagag cggcggtgga gtggtacagc ctgggcgatc cttgcggctt     60

gattgcaagg cgagcggaat aaccttcagc aacagtggga tgcactgggt aagacaagcg    120

ccaggcaagg ggctcgagtg ggtcgctgtc atctggtatg acggaagtaa acgatattac    180

gccgatagtg taaagggaag gtttacgatc agtagggata actctaaaaa tacgctcttt    240

cttcaaatga acagtcttcg agcagaagat acagcggtgt attattgtgc tactaatgac    300
```

-continued

```
gattattggg gccagggtac tctcgttacg gtaagctctg gtggaggagg aagtggtggc    360

ggaggtagtg gaggtggcgg ctccgggggt ggaggatccg agatagtact cacacaaagt    420

cctgctacgc tttcactctc ccctggagag agagctactc tctcatgccg agcctcccag    480

agtgtgagtt catatttggc gtggtaccag cagaagcccg gccaagcccc ccgattgctc    540

atatatgacg ccagtaatcg cgcgactggt atacctgccc ggtttagcgg aagtggatcc    600

gggacggact ttaccctgac aatttcttca ctggagcctg aagacttcgc cgtatattat    660

tgtcaacaat cctccaattg gccaagaact tttggccaag gaacgaaagt tgagataaaa    720


<210> SEQ ID NO 3
<211> LENGTH: 735
<212> TYPE: DNA
<213> ORGANISM: Artificial Sequence
<220> FEATURE:
<223> OTHER INFORMATION: gene encoding scFv PDL1(A)

<400> SEQUENCE: 3

gaagttcaac tggtggagtc tggagggggt ttggtgcagc caggcgggag tttgaggctc     60

agctgcgccg cctctggatt caccttctcc gatagctgga tccattgggt caggcaagcg    120

cctggtaaag ggttggagtg ggtcgcatgg atatctcctt atggagggtc tacatattat    180

gccgactctg tcaagggaag attcacgata tccgcagaca caagtaagaa tacagcatac    240

cttcaaatga actccctgcg cgctgaagac acggcggttt attattgcgc taggcggcac    300

tggccagggg gttttgacta ttggggtcaa ggtaccttgg tcacggtttc atccggcggc    360

ggtggtagcg gtggtggagg tagcgggggt ggtggaagtg gggtggagg ctcagacatc     420

caaatgacac aaagcccatc ctccctgagc gctagtgtgg gggaccgggt cacgataacc    480

tgccgggcta gccaagatgt gagcacagca gtcgcctggt atcagcagaa gcccgggaag    540

gccccaaaac tcctcatata ctctgcttct ttctctattc ccggtgtgcc ctctcgattc    600

tcaggcagtg ggtcaggaac cgacttcacg ctgaccatct caagtttgca gccggaagac    660

ttcgcaacgt attattgcca gcaatacctc taccatcctg ccactttcgg tcaggggacg    720

aaagtagaga ttaaa                                                     735


<210> SEQ ID NO 4
<211> LENGTH: 393
<212> TYPE: DNA
<213> ORGANISM: Artificial Sequence
<220> FEATURE:
<223> OTHER INFORMATION: sequence encoding hTERT targeting ribozyme

<400> SEQUENCE: 4

ggcaggaaaa gttatcaggc atgcacctgg tagctagtct ttaaaccaat agattgcatc     60

ggtttaaaag gcaagaccgt caaattgcgg gaaaggggtc aacagccgtt cagtaccaag    120

tctcagggga aactttgaga tggccttgca aagggtatgg taataagctg acggacatgg    180

tcctaaccac gcagccaagt cctaagtcaa cagatcttct gttgatatgg atgcagttca    240

cagactaaat gtcggtcggg gaagatgtat tcttctcata agatatagtc ggacctctcc    300

ttaatgggag ctagcggatg aagtgatgca acactggagc cgctgggaac taatttgtat    360

gcgaaagtat attgattagt tttggagtac tcg                                 393


<210> SEQ ID NO 5
<211> LENGTH: 1128
<212> TYPE: DNA
<213> ORGANISM: Artificial Sequence
```

<220> FEATURE:
<223> OTHER INFORMATION: sequence encoding HSVkt

<400> SEQUENCE: 5

```
atggcttcgt acccctgcca tcaacacgcg tctgcgttcg accaggctgc gcgttctcgc     60

ggccatagca accgacgtac ggcgttgcgc cctcgccggc agcaagaagc cacggaagtc    120

cgcctggagc agaaaatgcc cacgctactg cgggtttata tagacggtcc tcacgggatg    180

gggaaaacca ccaccacgca actgctggtg gccctgggtt cgcgcgacga tatcgtctac    240

gtacccgagc cgatgactta ctggcaggtg ctgggggctt ccgagacaat cgcgaacatc    300

tacaccacac aacaccgcct cgaccagggt gagatatcgg ccggggacgc ggcggtggta    360

atgacaagcg cccagataac aatgggcatg ccttatgccg tgaccgacgc cgttctggct    420

cctcatatcg ggggggaggc tgggagctca catgccccgc ccccggccct caccctcatc    480

ttcgaccgcc atcccatcgc cgccctcctg tgctacccgg ccgcgcgata ccttatgggc    540

agcatgaccc cccaggccgt gctggcgttc gtggccctca tcccgccgac cttgcccggc    600

acaaacatcg tgttgggggc ccttccggag gacagacaca tcgaccgcct ggccaaacgc    660

cagcgccccg gcgagcggct tgacctggct atgctggccg cgattcgccg cgtttacggg    720

ctgcttgcca atacggtgcg gtatctgcag ggcggcgggt cgtggcggga ggattgggga    780

cagctttcgg ggacggccgt gccgccccag ggtgccgagc cccagagcaa cgcgggccca    840

cgaccccata tcggggacac gttatttacc ctgtttcggg cccccgagtt gctggccccc    900

aacggcgacc tgtacaacgt gtttgcctgg gccttggacg tcttggccaa acgcctccgt    960

cccatgcacg tctttatcct ggattacgac caatcgcccg ccggctgccg ggacgccctg   1020

ctgcaactta cctccgggat ggtccagacc cacgtcacca cccccggctc cataccgacg   1080

atctgcgacc tggcgcgcac gtttgcccgg gagatggggg aggctaac                1128
```

<210> SEQ ID NO 6
<211> LENGTH: 22
<212> TYPE: DNA
<213> ORGANISM: Artificial Sequence
<220> FEATURE:
<223> OTHER INFORMATION: sequence encoding miR-122T

<400> SEQUENCE: 6

```
caaacaccat tgtcacactc ca                                               22
```

<210> SEQ ID NO 7
<211> LENGTH: 57
<212> TYPE: DNA
<213> ORGANISM: Artificial Sequence
<220> FEATURE:
<223> OTHER INFORMATION: sequence encoding p2a

<400> SEQUENCE: 7

```
gccacaaact tctctctgct aaagcaagca ggtgatgttg aagaaaaccc cgggcct         57
```

<210> SEQ ID NO 8
<211> LENGTH: 19
<212> TYPE: DNA
<213> ORGANISM: Artificial Sequence
<220> FEATURE:
<223> OTHER INFORMATION: RT primer(HSV-tk) of primer premix

<400> SEQUENCE: 8

```
agttagcctc ccccatctc                                                   19
```

-continued

```
<210> SEQ ID NO 9
<211> LENGTH: 25
<212> TYPE: DNA
<213> ORGANISM: Artificial Sequence
<220> FEATURE:
<223> OTHER INFORMATION: hTERT primer of primer premix

<400> SEQUENCE: 9

ggaattcgca gcgctgcgtc ctgct                                     25


<210> SEQ ID NO 10
<211> LENGTH: 30
<212> TYPE: DNA
<213> ORGANISM: Artificial Sequence
<220> FEATURE:
<223> OTHER INFORMATION: HSVkt primer of primer premix

<400> SEQUENCE: 10

gtgaggaccg tctatataaa cccgcagtag                                30


<210> SEQ ID NO 11
<211> LENGTH: 32
<212> TYPE: DNA
<213> ORGANISM: Artificial Sequence
<220> FEATURE:
<223> OTHER INFORMATION: portion of trans-spliced product's sequence in
      RZ001+_Ni condition

<400> SEQUENCE: 11

cagccgctgc gtcctgctaa aacgcccacc at                             32


<210> SEQ ID NO 12
<211> LENGTH: 31
<212> TYPE: DNA
<213> ORGANISM: Artificial Sequence
<220> FEATURE:
<223> OTHER INFORMATION: portion of trans-spliced product's sequence in
      RZ001+_AT condition

<400> SEQUENCE: 12

cagcgctgcg tcctggtaaa acgcccacca t                              31


<210> SEQ ID NO 13
<211> LENGTH: 24
<212> TYPE: DNA
<213> ORGANISM: Artificial Sequence
<220> FEATURE:
<223> OTHER INFORMATION: portion of trans-spliced product's sequence in
      RZ001+_PD1(I) condition

<400> SEQUENCE: 13

ctgcgtcctg taaaacgccc acca                                      24
```

CANCER-SPECIFIC TRANS-SPLICING RIBOZYME EXPRESSING IMMUNE CHECKPOINT INHIBITOR, AND USE THEREOF

CROSS REFERENCE TO RELATED APPLICATIONS

This application is a National Stage of International Application No. PCT/KR2022/001088 filed Jan. 21, 2022, claiming priority based on Korean Patent Application No. 10-2021-0010416 filed Jan. 25, 2021 and Korean Patent Application No. 10-2021-0193826 filed Dec. 31, 2021.

INCORPORATION BY REFERENCE OF SEQUENCE LISTING

The content of the electronically submitted sequence listing, file name: Q282840 SEQ LIS AS FILED 20230530.txtQ282840 SEQ LIST AS FILED.TXT; size: 7,7667,569 bytes; and date of creation: May 28Apr. 21, 2023, is hereby incorporated by reference in their entirety.

TECHNICAL FIELD

The present disclosure relates to a cancer-specific trans-splicing ribozyme expressing an immune checkpoint inhibitor in cancer cells and a use thereof.

BACKGROUND ART

As medical technology has advanced, cancer treatment technology has been continuously developed. In particular, recently, as a therapeutic effect of cancer immunotherapy developed using a human body immune system has been proven, a paradigm shift is in progress from anti-cancer therapy which had used conventional chemotherapeutic agents and targeted therapeutic agents to cancer immunotherapy using immunotherapeutic agents.

Conventional anti-cancer therapy is tumor resection through surgery. At this time, radiation therapy and chemotherapy are performed in parallel for the purpose of reducing the tumor volume before resection or killing remaining cancer cells after resection and preventing recurrence. Radiation therapy and chemotherapy, which are referred to as first-generation anticancer agents (since the 1970s), induce the death of cancer cells by interfering with a process of dividing and amplifying cancer cells indefinitely. However, radiation therapy and chemotherapy have side effects that induce the death of normal cells as well as cancer cells.

In the 2000s, targeted anticancer agents that selectively attack only cancer cells separately from normal cells were developed, and were referred to as second-generation anticancer agents that may significantly reduce side effects of first-generation anticancer agents. Targeted anticancer agents that act only on specific target proteins show therapeutic effects by acting only on proteins causing cancer to selectively inhibit cancer cells. Accordingly, since an induced protein or a protein exhibiting the therapeutic effect varies depending on a type of cancer, an anticancer agent suitable for a type of target protein needs to be used. The targeted anticancer agents have another limitation that cancer cells have a mechanism for acquiring resistance to the targeted anticancer agents. That is, since cancer cells themselves cause mutations so as not to be targeted by the targeted anticancer agents to acquire the avoidance performance of anticancer agents, the targeted anticancer agents may recognize cancer cells.

Cancer immunotherapy agents, third-generation anticancer agents, activate a human body immune system to enhance autoimmunity so that immune cells attack and eliminate cancer cells. The immune cells of which the ability to attack cancer cells is enhanced by cancer immunotherapy agents remember the cancer cells to be first attacked and continue to attack the cancer cells unless the cancer cells completely change their functions and properties.

The cancer immunotherapy agents may be largely classified into immune checkpoint inhibitors, immune cell therapy, therapeutic antibodies, and anticancer vaccines. The immune checkpoint inhibitor is a drug that attacks cancer cells by blocking the activity of immune checkpoint proteins involved in T cell suppression to activate T cells, and representatively, antibodies for recognizing CTLA 4, PD-1, PD-L1, and the like are used.

However, a response rate of cancer patients to cancer immunotherapy agents is still at the level of 15 to 45%, the response rate varies depending on a type of cancer and a patient, and side effects are increasingly being reported as the response rate affects various organs in vivo, such as the skin, gastrointestinal system, thyroid, and adrenal glands as well as cancer.

DISCLOSURE OF THE INVENTION

Technical Goals

An object of the present disclosure is to provide a trans-splicing ribozyme including two or more different cancer therapeutic genes including immune checkpoint inhibitor genes, and a vector and a gene delivery system capable of expressing the ribozyme.

In addition, the trans-splicing ribozyme may target a cancer-specific gene and actively act in cancer cells, and accordingly, an object of the present disclosure is to provide a use for cancer treatment of the ribozyme, the vector, or the gene delivery system.

However, technical objects of the present disclosure are not limited to the aforementioned purpose and other objects which are not mentioned may be clearly understood by those skilled in the art from the following description.

Technical Solutions

An aspect of the present disclosure provides a trans-splicing ribozyme targeting a cancer-specific gene, in which the ribozyme includes a target gene operably linked to the 3' exon, and the target gene is two or more anti-cancer therapeutic genes including an immune checkpoint inhibitor gene.

In an embodiment of the present disclosure, the trans-splicing ribozyme has a structure of 5'-trans-splicing ribozyme-cancer therapeutic gene-immune checkpoint inhibitor gene-3'.

In another embodiment of the present disclosure, one of the two or more anti-cancer therapeutic genes is a gene encoding an immune checkpoint inhibitor, and the other thereof is a cancer therapeutic gene distinguished from the gene and may be one selected from the group consisting of an agent-sensitizing gene, a proapoptotic gene, a cytostatic gene, a cytotoxic gene, a tumor suppressor gene, an antigenic gene, a cytokine gene, and an anti-angiogenic gene.

In yet another embodiment of the present disclosure, the agent-sensitizing gene may be Herpes Simplex Virus thymidine kinase (HSVtk) and may consist of or include a nucleotide sequence represented by SEQ ID NO: 5.

In yet another embodiment of the present disclosure, the cancer-specific gene may be one selected from the group consisting of telomerase reverse transcriptase (TERT) mRNA, alphafetoprotein (AFP) mRNA, carcinoembryonic antigen (CEA) mRNA, prostate-specific antigen (PSA) mRNA, cytoskeleton-associated protein 2 (CKAP2) mRNA, and mutant Rat sarcoma (RAS) mRNA.

According to one embodiment of the present disclosure, the trans-splicing ribozyme may target a TERT mRNA, and may consist of or include a nucleotide sequence represented by SEQ ID NO: 4.

As another embodiment of the present disclosure, the immune checkpoint inhibitor may be an inhibitor of CTLA-4, PD-1, PD-L1, PD-L2, LAG-3, BTLA, B7H3, B7H4, TIM3, KIR, TIGIT, CD47, VISTA, or A2aR.

As another embodiment of the present disclosure, the trans-splicing ribozyme may further include a sequence complementary to part or all of micro RNA-122a (miR-122a) at a 3'-terminal, may include a nucleotide sequence represented by SEQ ID NO: 6, and may include a sequence in which the sequence is repeated 2 to 10 times.

As another embodiment of the present disclosure, in the trans-splicing ribozyme, the immune checkpoint inhibitor gene, and the anti-cancer therapeutic genes other than the immune checkpoint inhibitor gene may be connected to a gene encoding a self-cleaving peptide.

As another embodiment of the present disclosure, the self-cleaving peptide may be P2A and may be encoded by a nucleotide sequence represented by SEQ ID NO: 7.

Another aspect of the present disclosure provides an expression vector capable of expressing the trans-splicing ribozyme.

As an embodiment of the present disclosure, the expression vector may further include a promoter operably linked to the ribozyme gene and the promoter may be a promoter operating tissue-specifically.

Yet another aspect of the present disclosure provides a gene delivery system containing the expression vector and a cell transformed with the expression vector.

Still another aspect of the present disclosure provides a pharmaceutical composition for the treatment of cancer including at least one selected from the group consisting of the trans-splicing ribozyme, the expression vector, and the gene delivery system as an active ingredient.

Still yet another aspect of the present disclosure provides a method for the treatment of cancer including administering at least one selected from the group consisting of the trans-splicing ribozyme, the expression vector, and the gene delivery system to a subject.

Still yet another aspect of the present disclosure provides a use of the trans-splicing ribozyme, the expression vector, and/or the gene delivery system for preparing an anticancer agent.

As an embodiment of the present disclosure, the pharmaceutical composition and the anticancer agent may be administered orally or in the form of injection through an intravenous, intraarterial, cancerous tissue, and/or subcutaneous route, and even in the method for the treatment of cancer, the administration to the subject may be performed through the routes.

As another embodiment of the present disclosure, the cancer may be at least one selected from the group consisting of liver cancer, glioblastoma, biliary tract cancer, lung cancer, pancreatic cancer, melanoma, bone cancer, breast cancer, colon cancer, stomach cancer, prostate cancer, leukemia, uterine cancer, ovarian cancer, lymphoma, and brain cancer.

As another embodiment of the present disclosure, the cancer may be immune checkpoint inhibitor resistant cancer.

Effects

According to the present disclosure, the trans-splicing ribozyme does not act on normal tissues, but is specifically expressed in cancer tissues, and thus is characterized to have high safety and excellent expression efficiency in the post-transcriptional level. In addition, one or more target genes are connected to the 3' exon of the ribozyme so that a cancer therapeutic gene and an immune checkpoint inhibitor are expressed together when applied in vivo to increase the action and activity of immune cells, thereby exhibiting a synergistic effect on anticancer efficacy together with the expressed anti-cancer therapeutic gene. Thus, the present disclosure can be effectively used in cancer treatment.

BEST MODE FOR CARRYING OUT THE INVENTION

In previous studies, the present inventors have prepared a trans-splicing ribozyme capable of treating cancer and a vector for expressing the ribozyme by using a trans-splicing ribozyme targeting a cancer-specific gene, specifically TERT mRNA to inhibit cancer proliferation and growth, and linking a target gene, particularly a cancer therapeutic gene to the ribozyme to induce the apoptosis of cancer cells.

In the previous studies, a trans-splicing ribozyme expression vector was named CRT-122T, and a basic structure thereof includes the following structure:

[5'-promoter–TERT targeting ribozyme–target gene (HSVtk)–miR-122T–3'].

A viral vector capable of expressing a vector added with SD/SA and WPRE sequences in CRT-122T was specified as RZ-001 (KR 10-2252423), and RZ-001 acts on various carcinomas to induce cell death and inhibit tumor growth, and thus can be applied to cancer treatment.

Figure 1:
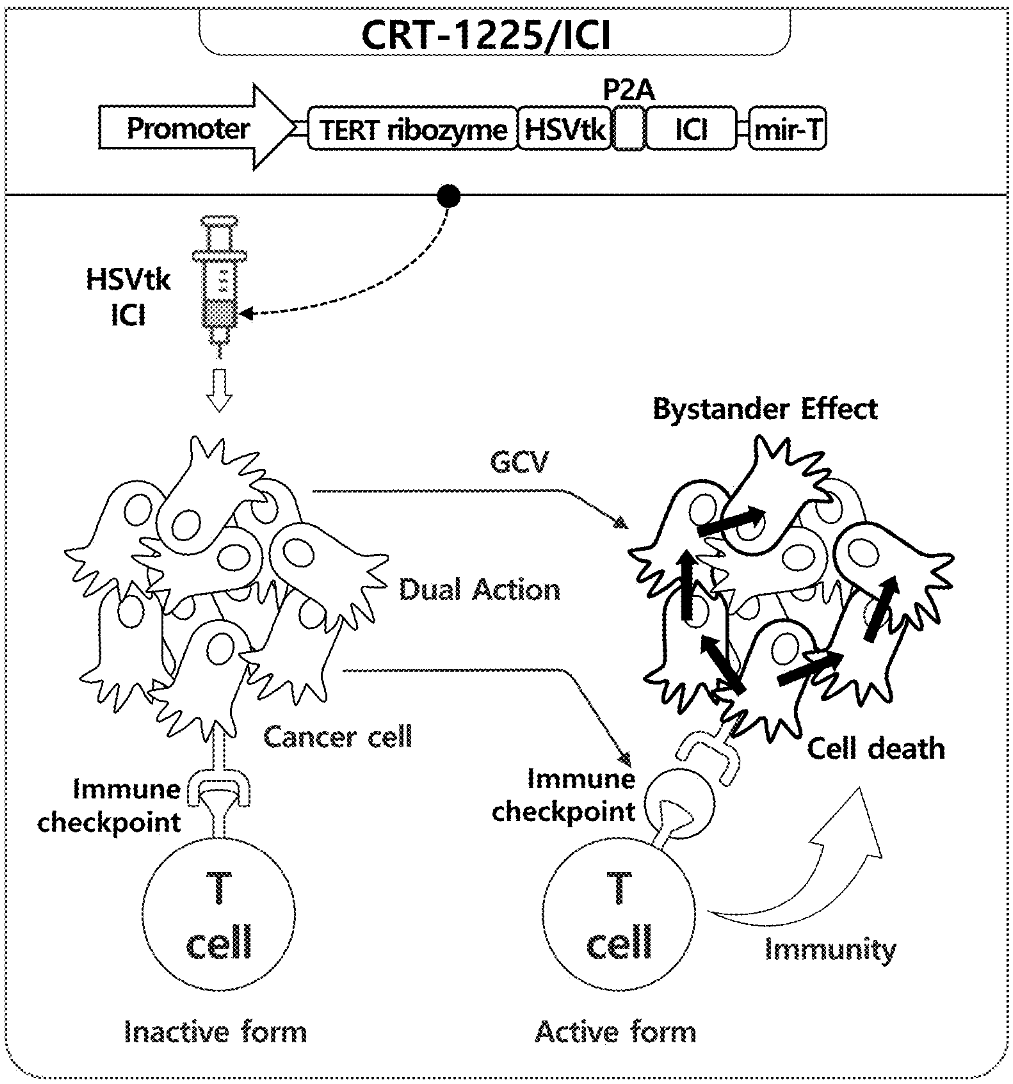
FIG. 1 is a diagram schematically illustrating a basic configuration and an anticancer mechanism of CRT-122T/ICI of the present disclosure. The CRT-122T/ICI is a vector capable of expressing a cancer therapeutic gene (HSVtk) and an immune checkpoint inhibitor (ICI) in a cancer-specific manner and expressing a TERT target trans-splicing ribozyme with a complementary sequence (mir-T) to miR-122a at a 3'-terminal.

Furthermore, in order to develop a trans-splicing ribozyme that can treat cancer more effectively in addition to the previous studies, the present inventors enlarged target genes expressed by the ribozyme into two types and included an immune checkpoint inhibitor gene in the target genes, and developed CRT-122T/ICI as a vector capable of expressing the ribozyme. The basic structure of the CRT-122T/ICI of the present disclosure is as follows (FIG. 1):

[5'-promoter–TERT targeting ribozyme–a target gene–self-cleaving peptide gene–immune checkpoint inhibitor gene–miR-122T–3'].

Meanwhile, in this specification, according to the immune checkpoint inhibitor encoded by CRT-122T/ICI, a target immune checkpoint protein or immune checkpoint inhibitor is indicated after "/". For example, a vector expressing Atezolizumab is indicated as CRT-122T/At.

Through a specific experiment, the present inventors showed that CRT-122T/ICI had cell death-inducing activity similar to that of CRT-122T in a liver cancer cell line, a brain tumor cell line, a lung cancer cell line, and a melanoma cell line (Embodiment 2). Furthermore, the present inventors prepared adenovirus (hereinafter referred to as "RZ-001+") expressing CRT-122T/ICI and confirmed the actions thereof in various cell lines through specific experiments.

Meanwhile, in the present specification, RZ-001+ was separately indicated as RZ-001+ (target immune checkpoint protein or immune checkpoint inhibitor) according to a type of loaded CRT-122T/ICI. For example, adenovirus including CRT-122T/At is indicated as RZ-001+ At.

Specifically, after infecting cancer cells with RZ-001+, the cell viability of the cancer cells was measured to confirm the degree of apoptosis according to RZ-001+ infection, and it was confirmed whether the introduction of CRT-122T/ICI according to the RZ-001+ infection expressed an antibody capable of blocking its function by binding to the immune checkpoint protein and then it was confirmed whether the antibody could be smoothly released and acted upon. As a result, it was confirmed that cell death of the cancer cells increased according to the RZ-001+ infection, the expression of the antibody increased, and the expressed antibody was sufficiently released (Embodiments 5 and 6).

Then, in order to confirm whether the anticancer activity of RZ-001+ confirmed in a cell experiment may be equally expressed in vivo, the present inventors prepared various cancer animal models to administer RZ-001+ and measure the size and weight of tumor. In particular, in order to evaluate the efficacy as a drug for treating brain tumor, a possibility of RZ-001+ as a brain tumor therapeutic agent was to be confirmed by preparing an orthotopic brain tumor model that simulated a microenvironment in the brain such as BBB. As a result, in both a liver cancer animal model and a brain tumor animal model, the tumor volume and weight were reduced according to RZ-001+ treatment. In particular, in a humanized liver cancer animal model, it was confirmed that an RZ-001+ At-administered group showed a reduction in tumor volume to a similar level compared to a co-administered group of RZ-001 and Atezolizumab, but showed lower in hepatotoxicity than that of the co-administered group, so that the RZ-001+ At-administered group could be provided as an anticancer agent with no or few side effects Embodiment 7). Furthermore, in an orthotopic brain tumor syngeneic model, an mRZ-001+ I (mCRT-122T scFvPD1 (I))-administered group showed more effective anticancer activity than an mRZ-001-administered group. In addition, the effective anticancer activity of RZ-001+ was confirmed even in a xenograft orthotopic brain tumor model in which human-derived brain tumor cells were transplanted. Therefore, the present inventors provide a trans-splicing ribozyme capable of targeting a cancer-specific gene in cells and expressing an immune checkpoint inhibitor and a cancer therapeutic material for cancer treatment.

Each component of the trans-splicing ribozyme of the present disclosure and the basic structure thereof are as follows:

[5'-ribozyme targeting cancer-specific gene–a target gene–self-cleaving peptide gene–immune checkpoint inhibitor gene–miR-122T–3'].

The trans-splicing ribozyme can complementarily bind to mRNA of a cancer-specific gene in a targeting cell, cleave the gene, and express transcripts of the target gene and beyond.

The trans-splicing ribozyme of the present disclosure includes a ribozyme targeting a cancer-specific gene, a target gene, a self-cleaving peptide gene, an immune checkpoint inhibitor gene, and miR-122T in the order of 5'—>3', each component may be operably linked in a direct or indirect manner within the scope of maintaining its function, and the trans-splicing ribozyme may further include a regulatory factor between respective components in order to specifically improve the function of the target gene.

The term "ribozyme" used in the present disclosure is a molecule composed of an RNA molecule that acts like an enzyme or a protein containing the RNA molecule, and is also called an RNA enzyme or catalytic RNA. As an RNA molecule with a clear tertiary structure, the ribozyme performs chemical reactions and has catalytic or autocatalytic properties. It is known that some ribozymes cleave self- or other RNA molecules to inhibit the activity, and other ribozymes catalyze the activity of aminotransferase of ribosomes. These ribozymes may include a hammerhead ribozyme, a VS ribozyme, a hairpin ribozyme, and the like.

The ribozyme according to the present disclosure may not only exhibit a selective anticancer effect by inhibiting the activity of a cancer-specific gene through the trans-splicing reaction of Group I introns, but also may be expressed in a form conjugated with a cancer therapeutic gene to activate the anti-cancer therapeutic gene. Therefore, any type of ribozyme may be used as long as the ribozyme exhibits characteristics capable of inactivating cancer-specific genes and activating anti-cancer therapeutic genes.

The ribozyme according to the present disclosure may be preferably a ribozyme targeting hTERT mRNA as described above, and may serve to target cancer cells in which hTERT is overexpressed, and specifically cleave hTERT mRNA to inhibit the expression and specifically express the target gene.

As used herein, the term "trans-splicing" means connecting RNAs from different genes to each other. Preferably, an hTERT target trans-splicing group I ribozyme verified for trans-splicing ability by recognizing mRNA of cancer-specific hTERT may be used.

The term "target gene" used in the present disclosure refers to a gene which is connected to mRNA of a cancer-specific gene by the ribozyme to induce the expression.

The target gene according to the present disclosure may preferably be a cancer therapeutic gene or a reporter gene, and most preferably an anti-cancer therapeutic gene.

As used herein, the term "anti-cancer therapeutic gene" refers to a polynucleotide sequence encoding a polypeptide that exhibits a therapeutic effect when expressed in cancer cells. The cancer therapeutic gene may be expressed in a conjugated form with the ribozyme or independently expressed to exhibit anticancer activity. These anti-cancer therapeutic genes may be preferably one or more selected from the group consisting of an agent-sensitizing gene, a proapoptotic gene, a cytostatic gene, a cytotoxic gene, a tumor suppressor gene, an antigenic gene, a cytokine gene, and an anti-angiogenic gene, and most preferably an agent-sensitizing gene.

In the present disclosure, the cancer therapeutic gene may be used alone or two or more genes may be used in combination.

The agent-sensitizing gene according to the present disclosure is a gene encoding an enzyme that converts a non-toxic prodrug into a toxic substance, and is also called a suicide gene because cells introduced with the gene are dead. That is, when the non-toxic prodrug is systemically administered to normal cells, the prodrug is converted into a toxic metabolite only in cancer cells to change the sensitivity to the agent, thereby destroying the cancer cells. The agent-sensitizing gene may be preferably a Herpes simplex virus-thymidine kinase (HSVtk) gene using ganciclovir as a prodrug, or a cytosine deaminase (CD) gene of *E. coli* using 5-fluorocytosine (5-FC) as a prodrug, most preferably an HSVtk gene.

The proapoptotic gene according to the present disclosure refers to a nucleotide sequence that induces programmed cell death when expressed. The proapoptotic genes known to those skilled in the art may include p53, adenovirus E3-11.6K (derived from Ad2 and Ad5) or adenovirus E3-10.5K (derived from Ad), adenovirus E4 genes, a p53 pathway gene, and a gene encoding caspase.

The cytostatic gene according to the present disclosure refers to a nucleotide sequence that is expressed in cells and stops a cell cycle during the cell cycle. Examples thereof include p21, a retinoblastoma gene, an E2F-Rb fusion protein gene, genes (e.g., p16, p15, p1,8 and p19) encoding a cyclin-dependent kinase inhibitor, a growth arrest specific homeobox (GAX) gene, etc., but are not limited thereto.

The cytotoxic gene according to the present disclosure refers to a nucleotide sequence that is expressed in cells to exhibit a toxic effect. Examples thereof include nucleotide sequences encoding Pseudomonas exotoxin, ricin toxin, diphtheria toxin, and the like, but are not limited thereto.

The tumor suppressor gene according to the present disclosure refers to a nucleotide sequence capable of suppressing a tumor phenotype or inducing apoptosis by being expressed in a target cell. Representatively, the tumor suppressor gene may include tumor necrosisfactor-α (TNF-α), p53 gene, APC gene, DPC-4/Smad4 gene, BRCA-1 gene, BRCA-2 gene, WT-1 gene, retinoblastoma gene, MMAC-1 gene, adenomatous polyposis coil protein, deleted colon cancer (DCC) gene, MMSC-2 gene, NF-1 gene, nasopharyngeal cancer suppressor gene located on chromosome 3p21.3, MTS1 gene, CDK4 gene, NF-1 gene, NF-2 gene, VHL gene, or sPD-1 (programmed death-1).

The antigenic gene according to the present disclosure refers to a nucleotide sequence that is expressed in a target cell to produce a cell surface antigenic protein that may be recognized by an immune system. Examples of the antigenic gene known to those skilled in the art may include carcinoembryonic antigen (CEA) and p53.

The cytokine gene according to the present disclosure refers to a nucleotide sequence that is expressed in a cell to produce cytokines. Representatively, the cytokine gene may include GMCSF, interleukins IL-1, IL-2, IL-4, IL-12, IL-10, IL-19, and IL-20, interferons α, β, and γ (interferon α-2b), fusions such as interferon α-2α-1, etc.

The anti-angiogenic gene according to the present disclosure refers to a nucleotide sequence that is expressed to release an anti-angiogenic factor out of the cell. Examples thereof may include angiostatin, vascular endothelial growth factor (VEGF) inhibitor, endostatin, and the like.

As used herein, the term "HSVtk (Herpes simplex virus-thymidine kinase)" refers to a thymidine kinase derived from a herpes simplex virus. This enzyme is a representative example of an agent-sensitizing gene that converts a non-toxic prodrug into a toxic substance to cause the cells transfected with the gene to die. In the present disclosure, the HSVtk gene is expressed in a form conjugated to the ribozyme according to the present disclosure and may be used as a cancer therapeutic gene exhibiting anticancer activity. These HSVtk genes may be preferably disclosed in genbank registration Nos. AAP13943, P03176, AAA45811, P04407, Q9QNF7, KIBET3, P17402, P06478, P06479, AAB30917, P08333, BAB84107, AAP13885, AAL73990, AAG40842, BAB11942, NP_044624, NP_044492, CAB06747, and the like.

As used herein, the term "reporter gene" is a gene used to monitor the introduction of a recombinant vector or the expression efficiency of a ribozyme according to an embodiment of the present disclosure, and genes that can be monitored without damaging infected cells or tissues may be used as the reporter gene without limitation. Preferably, the reporter gene may be luciferase, green fluorescent protein (GFP), modified green fluorescent protein (mGFP), enhanced green fluorescent protein (EGFP), red fluorescent protein (RFP), modified red fluorescent protein (mRFP), enhanced red fluorescent protein (ERFP), blue fluorescent protein (BFP), enhanced blue fluorescent protein (EBFP), yellow fluorescent protein (YFP), enhanced yellow fluorescence protein (EYFP), cyan fluorescent protein (CFP), or enhanced cyan fluorescent protein (ECFP).

By inserting the reporter gene into the target gene, the expression level of the cancer cell-specific ribozyme may be observed, and particularly, the ribozyme of the present disclosure includes a promoter and a microRNA target site, so that the ribozyme is not expressed in normal cells, but may be specifically expressed in cancer cells. It is obvious to those skilled in the art that it can be applied to diagnose whether cancer has occurred in a specific tissue using the ribozyme.

In the present specification, a nucleotide sequence complementary to part or all of miR-122 is referred to as a microRNA-122 target site (miR-122T). In the present disclosure, as long as the miR-122T may complementarily bind to miR-122 to form dsRNA, there may be differences in specific sequences. The miR-122T may include a nucleotide sequence complementary to part or all of miR-122 one or more times, for example, 1 to 10 times, preferably 1 to 5 times, more preferably 1 time to 3 times repeatedly. The miR-122 is normally expressed in normal hepatocytes, but the expression level thereof is reduced in liver cancer cells. Using this, it is possible to develop a therapeutic agent with increased sensitivity and specificity for liver cancer cells, and in the present disclosure, a nucleic acid sequence recognizing miR-122 is connected to a ribozyme to which a target gene is connected to perform the expression of a liver cancer cell-specific ribozyme.

The term "cancer-specific gene" used in the present disclosure refers to a gene that is specifically expressed or remarkably overexpressed only in cancer cells. The cancer-specific gene may add a feature that allows the ribozyme according to the present disclosure to act in a cancer-specific manner. Such a cancer-specific gene may be preferably telomerase reverse transcriptase (TERT) mRNA, alphafetoprotein (AFP) mRNA, carcinoembryonic antigen (CEA) mRNA, prostate-specific antigen (PSA) mRNA, cytoskeleton-associated protein 2 (CKAP2) mRNA, or mutant Rat sarcoma (RAS) mRNA, more preferably telomerase reverse transcriptase (TERT) mRNA, and most preferably a human telomerase reverse transcriptase (hTERT) mRNA sequence. The trans-splicing ribozyme of the present disclosure induces trans-splicing targeting the cancer-specific gene to express a target gene connected to the ribozyme, thereby confirming a cell death-inducing effect in a glioblastoma cell line, a melanoma cell line, a liver cancer cell line, and a lung cancer cell line.

As used herein, the term "TERT (Telomerase reverse transcriptase)" is one of the most important enzymes that regulate the immortality and proliferation ability of cancer cells, and refers to an enzyme that inhibits the aging of cells by forming a telomere structure on a chromosome to protect the chromosome end. In normal cells, whenever the cells divide, the lengths of the telomeres decrease little by little, and eventually, a genetic substance is lost and the cells die. However, in cancer cells, this enzyme continuously elongates telomeres, so that the cells do not die due to a cycle, and the enzyme directly contributes to the immortality of cancer cells, which is known as a major obstacle to cancer treatment. In the present disclosure, hTERT mRNA may be used as a cancer-specific gene, but is not limited thereof.

As used herein, the term "gene delivery system" refers to a system capable of increasing expression efficiency by increasing the delivery efficiency of a target gene and/or nucleic acid sequence into a cell, and may be classified into a virus-mediated system and a non-viral system.

The virus-mediated system uses viral vectors such as a retroviral vector and an adenovirus vector, and is known to have relatively higher intracellular gene delivery efficiency than that of the non-viral system by using an unique intracellular penetration mechanism of viruses that infect human cells. In addition, after entering the cell, the non-viral vector has a problem in that an endosome is fused with the lysosome and then the genes are degraded in the endolysosome, but the viral vector has an advantage of having high gene delivery efficiency due to low gene loss caused by a mechanism for delivering the gene into the nucleus without passing through the lysosome.

Viral vectors that can be used in the present disclosure may be vectors derived from retroviruses, adenoviruses, adeno-associated viruses, and the like, as described above in the recombinant vector. These viral vectors may be assembled into viral particles and then introduced into cells by a transduction method such as infection.

In an embodiment of the present disclosure, a recombinant adenovirus including the above-described recombinant vector was designed as an example of a gene carrier. That is, the recombinant adenovirus performs a function of delivering a recombinant vector expressing a trans-splicing ribozyme specific for a cancer-specific gene into a target cell (e.g., cancer cell), and the recombinant vector delivered into the cell is expressed by an intracellular transcription system. The expressed trans-splicing ribozyme may insert a target gene connected to the ribozyme into transcripts of the cancer-specific gene that are abundant in cancer cells.

In the present specification, RZ-001 means adenovirus expressing CRT-122T, and RZ-001+ means adenovirus expressing CRT-122T/ICI.

The non-viral system is a method using a cationic lipid carrier, a cationic polymer carrier, or the like as a delivery medium for nucleic acids and/or genes, or using an electroporation method.

The cationic lipid carrier is a method of forming a complex with a gene as a negative charge and an expression vector or nucleic acid containing the gene using a positive charge of nanometer-sized liposomes or lipid nanoparticles mainly composed of cationic lipids and then delivering the complex into cells by phagocytosis. The complex delivered into the cell is first delivered from the endosome to the lysosome and then released into the cytoplasm to be expressed. The cationic polymer carrier delivers a gene in a similar manner to a cationic lipid carrier, except for using a polymer instead of lipids, and a representative cationic polymer includes polyethyleneimine, poly-L-lysine, chitosan, and the like.

Accordingly, a complex formed by combining the recombinant vector of the present disclosure with the cationic lipid carrier or the cationic polymer carrier may be used as a gene carrier.

In the present disclosure, the gene delivery system includes the above-described recombinant vector, and both a virus-mediated system and a non-viral system may be used, but it is preferable to use a virus-mediated system.

As used herein, the term "vector" is an expression vector capable of expressing a target gene in a suitable host cell, and refers to a gene construct containing a regulatory element operably linked to express a gene insert contained in the vector.

As used herein, the term "operably linked" means that a nucleic acid sequence encoding a target protein is functionally connected to a nucleic acid expression regulatory sequence to perform a general function. In the ribozyme or vector of the present disclosure, each component is considered to be operably linked to each other unless specified as being directly connected.

For example, when operably connecting a ribozyme coding sequence to a promoter, the expression of the ribozyme coding sequence is under the influence or control of the promoter. Two nucleic acid sequences (a ribozyme-coding sequence and a promoter site sequence at the 5' end of the sequence) are operably linked when the ribozyme-coding sequence is transcribed by inducing the action of the promoter, and the linkage characteristic between the two sequences does not induce a frameshift mutation, and the expression regulatory sequence may be considered to be operably linked if the expression of the ribozyme is not inhibited. The operable linkage with the recombinant vector may be manufactured using a gene recombination technique well-known in the art, and site-specific DNA cleavage and linkage may use enzymes and the like which are generally known in the art.

The vector according to the present disclosure includes a signal sequence or a leader sequence for membrane targeting or release in addition to expression regulatory elements such as a promoter, an operator, an initiation codon, a termination codon, a polyadenylation signal, and an enhancer, and may be variously manufactured according to a purpose. In addition, the vector of the present disclosure may further include a regulatory factor capable of increasing the expression level of the trans-splicing ribozyme in cells. Non-limiting examples of the regulatory factor for increased expression of the ribozyme include a splicing donor/splicing acceptor (SD/SA) sequence and WPRE. The promoter of the vector may be constitutive or inductive. Further, the expression vector includes a selective marker for selecting a host cell containing a vector and a replicable expression vector may include a replication origin. The vector may be self-replicated or integrated into the host DNA.

The vector according to the present disclosure may be preferably a plasmid vector, a cosmid vector, a viral vector, or the like, and most preferably a viral vector. The viral vector may be preferably vectors derived from retrovirus, such as human immunodeficiency virus (HIV), murine leukemia virus (MLU), avian sarcoma/leucosis virus (ASLV), spleen necrosis virus (SNV), Rous sarcoma virus (RSV), mouse mammary tumor virus (MMTV), adenovirus, adeno-associated virus (AAV), or herpes simplex virus (HSV), but is not limited thereto. The recombinant vector according to the present disclosure may most preferably be a recombinant adenoviral vector.

As used herein, the term "promoter" is involved in the binding of RNA polymerase to initiate transcription with a portion of DNA. Generally, the promoter is adjacent to the target gene and located upstream of the target gene, and is a site to which RNA polymerase or a transcription factor which is a protein inducing RNA polymerase is bound to induce the enzyme or protein to be located at a correct transcription starting site. That is, the promoter is located at a 5' site of a gene to be transcribed in a sense strand and induces RNA polymerase to bind to the corresponding position directly or through a transcription factor to initiate mRNA synthesis for the target gene, and has a specific gene sequence.

On the other hand, the trans-splicing ribozyme of the present disclosure has cell death-inducing activity in various carcinomas and has no or very low hepatotoxicity, so that the trans-splicing ribozyme can be used for cancer treatment.

As used herein, the term "cancer" means a condition in which a problem in a regulatory function of normal cell division, differentiation, and apoptosis occurs, and thus the cells are abnormally excessively proliferated and invade surrounding tissues and organs to form a lump and destroy or transform an existing structure.

The cancer according to the present disclosure may be preferably liver cancer, glioblastoma, biliary tract cancer, lung cancer, pancreatic cancer, melanoma, bone cancer, breast cancer, colon cancer, stomach cancer, prostate cancer, leukemia, uterine cancer, ovarian cancer, lymphoma, or brain cancer, more preferably liver cancer, lung cancer, melanoma, glioblastoma, and/or biliary tract cancer, and most preferably liver cancer and/or brain cancer.

In addition, in the cancer according to the present disclosure, preferably, the copy number (expression level) of miR-122 expressed in cancer tissues may be less than 100 times the copy number of the ribozyme expressed in cancer tissues by the pharmaceutical composition.

On the other hand, the present inventors compared the expression level of the hTERT target ribozyme with miR-122T capable of inducing cell death with the expression level of miR-122 in cells in previous studies, and as a result, it was confirmed that as the ratio of miR-122 to the ribozyme was increased, the expression of the ribozyme was reduced and the cell death-inducing effect was reduced. Accordingly, the injection amount of adenovirus expressing the ribozyme may be determined by inferring the amount of the ribozyme to exhibit the anticancer effect according to the expression level of miR-122 in cancer tissues. Specifically, if the minimum copy number of miR-122 is about 100 times or more than the ribozyme copy number, the function (expression) of the ribozyme having an miR-122 target site is attenuated, so that it can be seen that high anticancer efficacy can be obtained if the copy number of miR-122 expressed in cancer tissues is less than 100 times the copy number of the ribozyme expressed in cancer tissues by the pharmaceutical composition according to the present disclosure.

In addition, the cancer according to the present disclosure may preferably be a cancer in which miR-122 is not substantially expressed in cancer tissues. The "cancer in which miR-122 is not substantially expressed in cancer tissues" means a cancer in which miR-122 is expressed in cancer tissues, but the copy number of miR-122 expressed in cancer tissues is low enough not to substantially affect the function of the ribozyme having the miR-122 target site.

Through previous studies, the present inventors have found that the anti-cancer efficacy of the ribozyme according to the present disclosure was confirmed in colorectal cancer, glioblastoma, melanoma, cervical cancer, lung cancer, osteosarcoma, breast cancer, and biliary tract cancer cell lines in which miR-122 is not substantially expressed in cancer tissues.

In the present disclosure, the immune checkpoint inhibitor (ICI) performs an inhibition function of binding of PD-L1 and PD-1 to maintain the immune function of T cells and inhibits PD-1 or PDL-1 that hampers the activity of T-cells infiltrated into tumors to maximize the activity of T-cells, thereby increasing the anticancer effect. In a specific experiment, according to the present disclosure, the expression sequences of immune checkpoint inhibitors represented by SEQ ID NOs: 1 to 3 are included in the ribozyme of the present disclosure to induce expression in cells and confirm its function, but are not limited as long as the immune checkpoint inhibitor is targeting an immune checkpoint protein for T-cell activity.

As used herein, the term "prevention" refers to any action that suppresses cancer or delays the onset by administering a combination or the pharmaceutical composition according to the present disclosure.

As used herein, the term "treatment" refers to any action that improves cancer or changes its symptoms beneficially by administering a combination or the pharmaceutical composition according to the present disclosure.

The pharmaceutical composition of the present disclosure may include a pharmaceutically acceptable carrier, an excipient, or a diluent. Examples of the pharmaceutically acceptable carrier, the excipient, and the diluent that may be used in the pharmaceutical composition of the present disclosure may include lactose, dextrose, sucrose, sorbitol, mannitol, xylitol, erythritol, maltitol, starch, acacia rubber, alginate, gelatin, calcium phosphate, calcium silicate, calcium carbonate, cellulose, methylcellulose, polyvinylpyrrolidone, water, methylhydroxybenzoate, propylhydroxybenzoate, talc, magnesium stearate, mineral oils, or the like.

The pharmaceutical composition of the present disclosure may be administered orally or parenterally depending on a desired method, but is preferably administered parenterally.

According to one embodiment of the present disclosure, the pharmaceutical composition according to the present disclosure may be directly administered intravenously, intraarterially, intratumorally, or subcutaneously, or administered as an injection. The injection according to the present disclosure may be a form dispersed in a sterile medium so as to be used as it is when administered to a patient, or may also be administered after dispersing in an appropriate concentration by adding distilled water for injection during administration. In addition, when prepared as an injection, the pharmaceutical composition may be mixed with buffers, preservatives, analgesics, solubilizers, tonicity agents, stabilizers, etc., and may be prepared in unit dosage ampoules or multiple dosage forms.

A dose of the pharmaceutical composition of the present disclosure varies according to the condition and weight of a patient, the degree of a disease, a drug form, and the route and period of administration, but may be properly selected by those skilled in the art. Meanwhile, the pharmaceutical composition according to the present disclosure may be used alone or in combination with auxiliary treatment methods such as surgical treatment.

Hereinafter, embodiments will be described in detail with reference to the accompanying drawings. However, since various modifications may be made to the embodiments, the scope of the present disclosure is not limited or restricted by these embodiments. It should be understood that all modifications, equivalents, and substitutes for the embodiments are included in the scope of the present disclosure.

The terms used in the embodiments are used for the purpose of description only, and should not be construed to be limited. The singular expression includes the plural expression unless the context clearly dictates otherwise. In the present specification, it should be understood that term "comprising" or "having" indicates that a feature, a number, a step, an operation, a component, a part, or the combination thereof described in the specification is present, but does not exclude a possibility of presence or addition of one or more other features, numbers, steps, operations, components, parts, or combinations thereof, in advance.

Unless otherwise contrarily defined, all terms used herein including technological or scientific terms have the same meanings as those generally understood by a person with ordinary skill in the art to which embodiments pertain. Terms which are defined in a generally used dictionary should be interpreted to have the same meaning as the meaning in the context of the related art, and are not interpreted as ideal or excessively formal meanings unless otherwise defined in the present application.

In addition, in the description with reference to the accompanying drawings, the same reference numerals are designated to the same components regardless of reference numerals and a duplicated description thereof will be omitted. In describing the embodiments, a detailed description of related known technologies will be omitted if it is determined that they unnecessarily make the gist of the embodiments unclear.

Embodiment 1: Preparation of Trans-Splicing Ribozyme Expressing Immune Checkpoint Inhibitor A recombinant vector modified from a previously prepared trans-splicing ribozyme was designed. Specifically, the recombinant vector included a CMV promoter, targeted a site including uridine+21 of hTERT mRNA, and had an anti-sense of 326 nucleotides in length, had miR-122T, miR 122 target site, and additionally introduced a nucleic acid sequence P2A encoding a peptide cleavage site and an immune checkpoint inhibitor expression sequence to an end of HSV-tk in a trans-splicing ribozyme expression construct having HSV-tk as a therapeutic gene.

As the immune checkpoint inhibitor, single chain variable fragment PD1 (scFvPD1) or scFvPDL1 prepared by applying PD1 antibody or PDL1 antibody sequences known in the art were used. In the present disclosure, the scFvPD1 used two antibodies with differences in amino acid sequence, and the genes encoding each of the two antibodies were shown in SEQ ID NOs: 1 and 2 (hereinafter, referred to as scFvPD1 (I) and scFvPD1(N), respectively). In addition, a gene sequence encoding scFvPDL1 was shown in SEQ ID NO: 3 (hereinafter referred to as scFvPDL1 (A)).

A FLAG Tag sequence was introduced at the end of the immune checkpoint inhibitor, and 3 copies of miR-122T were inserted at a 3' terminal of the construct to regulate the expression of the ribozyme by miR-122.

Meanwhile, except only that the ribozyme targeted a site containing uridine +67 of mouse TERT (mTERT) mRNA and had an antisense of 100 nucleotides in length, a recombinant vector (mCRT-122T/immune checkpoint inhibitor) including the same configuration as above was also prepared.

Figure 2:
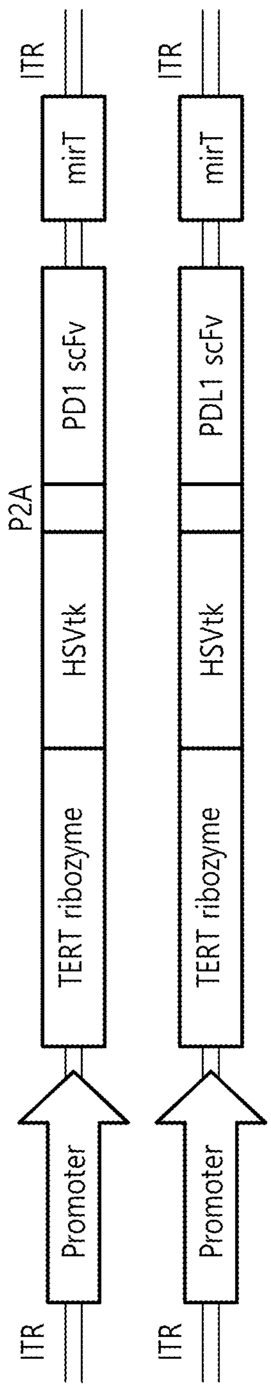
FIG. 2 is a diagram schematically illustrating a configuration of CRT-122T/ICI expressing PD1scFv (scFv for PD1) or PDL1scFv (scFv for PDL1).

The designed expression vector of the trans-splicing ribozyme was named mCRT-122T/ICI, and its vector structure was shown in FIG. 2.

Meanwhile, in an experiment below, the activities of mCRT-122T prepared in previous studies and mCRT-122T/ICI were compared and confirmed, and the structure of mCRT-122T was as follows:

5'-CMV promoter–mTERT ribozyme–HSVtk–miR-122T (3X)–3'.

Meanwhile, adenovirus expressing the CRT-122T/ICI vector was named RZ-001+, adenovirus expressing the mCRT-122T/ICI vector was named mRZ-001+, respectively, and adenovirus expressing the CRT-122T vector was named RZ-001.

Embodiment 2. Confirmation of Equivalence with RZ-001 Through RZ-001+ Cell Death Induction Experiment 2-1. Confirmation of Equivalence in Human Liver Cancer Cell Line In order to compare the equivalence of RZ-001 prepared in previous studies, a cell death induction experiment was performed in a human liver cancer cell line.

Specifically, SNU398 and Hep3b were dispensed at $1\times10^4$ cells/well/100 μl in a 96-well plate, the used medium was removed on the next day, and then in an FBS 2% medium, RZ-001 and RZ-001+ were treated at different multiplicities of infection (MOI) (0.01 to 10 MOI). After 24 hours of virus treatment, 100 μM GCV was treated three times at 2-day intervals. Finally, on the next day after GCV treatment, each well was treated with 10 μl of EZ-Cytox regent (DOGEN, EZ-1000), incubated at 37° C., and then absorbance was measured at Abs 450 nm.

Figure 3:
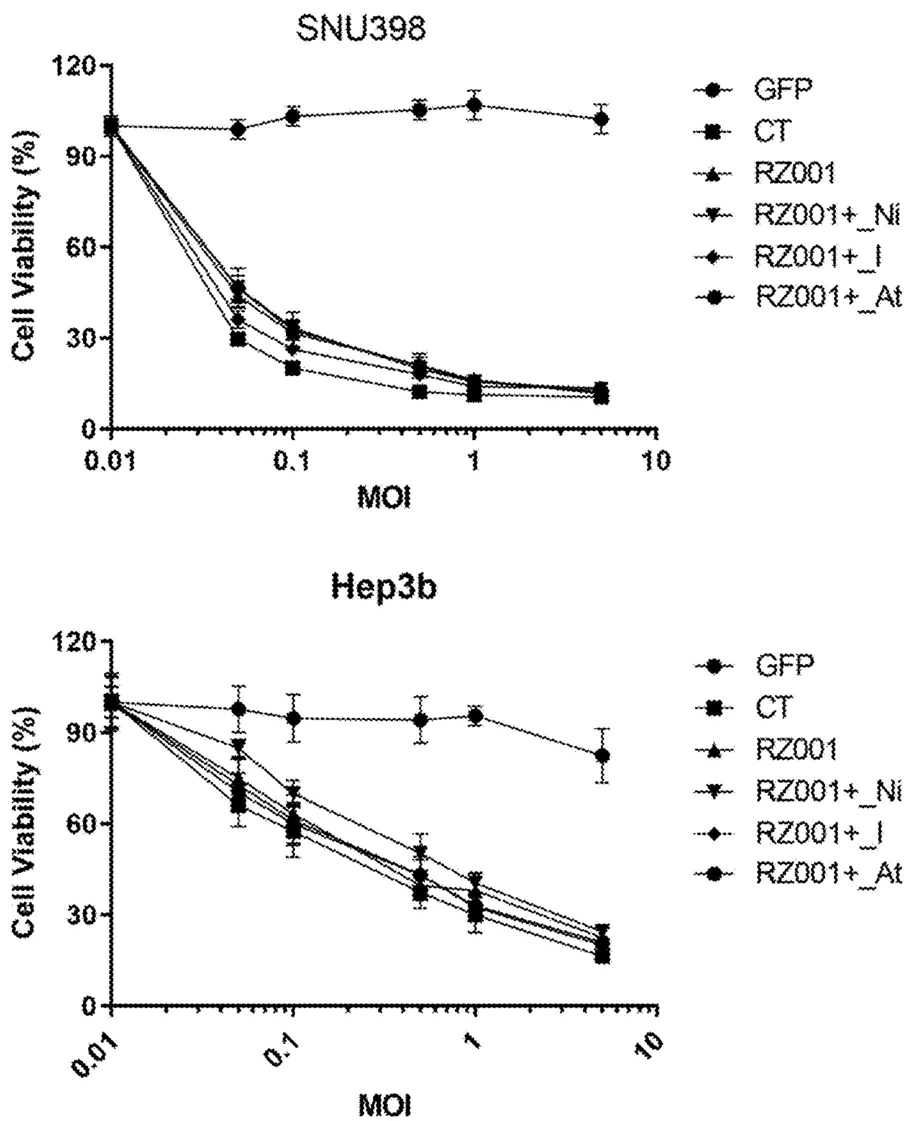
FIG. 3 illustrates a result of confirming the equivalence of RZ-001 by confirming the cell death-inducing activity of various RZ-001+ in a liver cancer cell line. RZ-001+ is a viral vector capable of expressing a vector including CRT-122T/ICI. RZ-001 is a vector capable of expressing a cancer therapeutic gene (HSVtk) in a cancer-specific manner and expressing an hTERT target trans-splicing ribozyme with a complementary sequence (mir-T) to miR-122a at a 3'-terminal (Registration No. 10-2252423).

As a result, it was confirmed that apoptosis of liver cancer cells increased as the concentration of RZ-001 or RZ-001+ treatment increased, and it was found that there was no problem with the cell death-inducing activity by a hTERT targeting ribozyme according to the addition of the immune checkpoint inhibitor gene. In addition, at an in vitro cell line level, which was an absence condition of an immune system, it was found that RZ-001+ showed equal activity to RZ-001 by the hTERT targeting ribozyme (FIG. 3).

2-2. Confirmation of Equivalence in Human Brain Tumor Cell Line

A human brain tumor cell line U87MG was dispensed at $1\times10^4$ cells/well/100 μl in a 96-well plate, the used medium was removed on the next day, and then in an FBS 2% medium, RZ-001 and RZ-001+ were treated at various concentrations (0.01 to 10 MOI), respectively. After 24 hours of virus treatment, 100 μM GCV was treated three times at 2-day intervals. Finally, on the next day after GCV treatment, each well was treated with 10 μl of EZ-Cytox regent (DOGEN, EZ-1000), incubated at 37° C., and then absorbance was measured at Abs 450 nm.

Mock did not include a transgene and thus was used as adenovirus control that did not express the transgene, and was used as a negative control to confirm that there was no non-specific cell death induction by adenovirus infection. In addition, CT was CMV-HSVtk, which was used as a positive control to confirm cell death induction caused by GCV phosphorylation by HSVtk.

Figure 4:
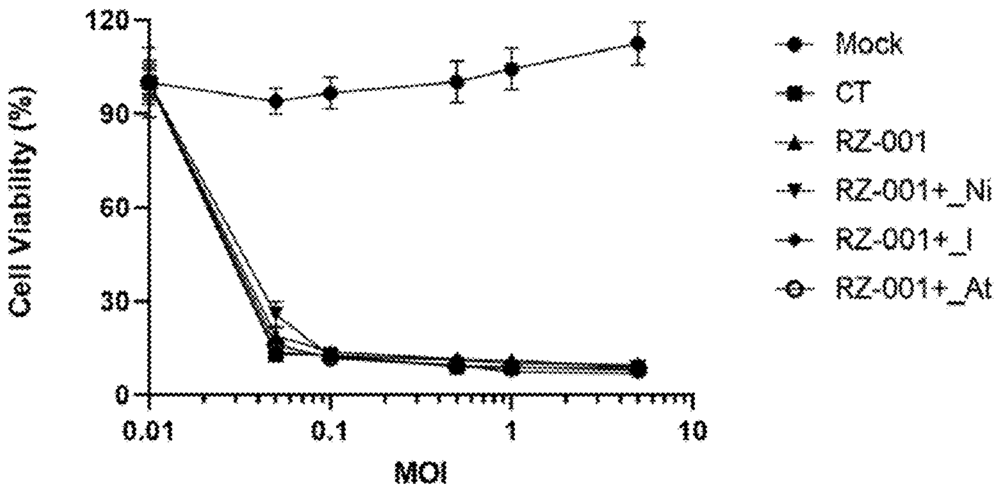
FIG. 4 illustrates a result of confirming the equivalence of RZ-001 by confirming the cell death-inducing activity of various RZ-001+ in a brain tumor cell line.

From an absorbance measurement result, it was confirmed that cell death was induced in RZ-001 and all RZ-001+-treated groups. From the above, it can be seen that all RZ-001+ exhibited cell death-inducing activity in brain tumor cells, and in particular, all RZ-001+ exhibited the same effect as RZ-001 at 0.5 MOI or higher (FIG. 4).

2-3. Confirmation of Equivalence in Lung Cancer Cell Line and Melanoma Cell Line An apoptotic effect of RZ-001+ was confirmed in a human lung cancer cell line, A549 cell line and human melanoma cell lines A375P and A375SM. Each cell line was dispensed in a 96-well plate at $1\times10^4$ cells/well/100 μl, and on the next day, the used medium was exchanged with a FBS 2% medium, and then RZ-001+ was treated at different concentrations. From the next day of the virus treatment, GCV was treated at a concentration of 100 μM three times at 2-day intervals, and after 24 hours of the last GCV treatment, each well was treated with 10 μl of EZ-Cytox regent (DOGEN, EZ-1000), incubated at 37° C., and absorbance was measured at Abs 450 nm.

Figure 5:
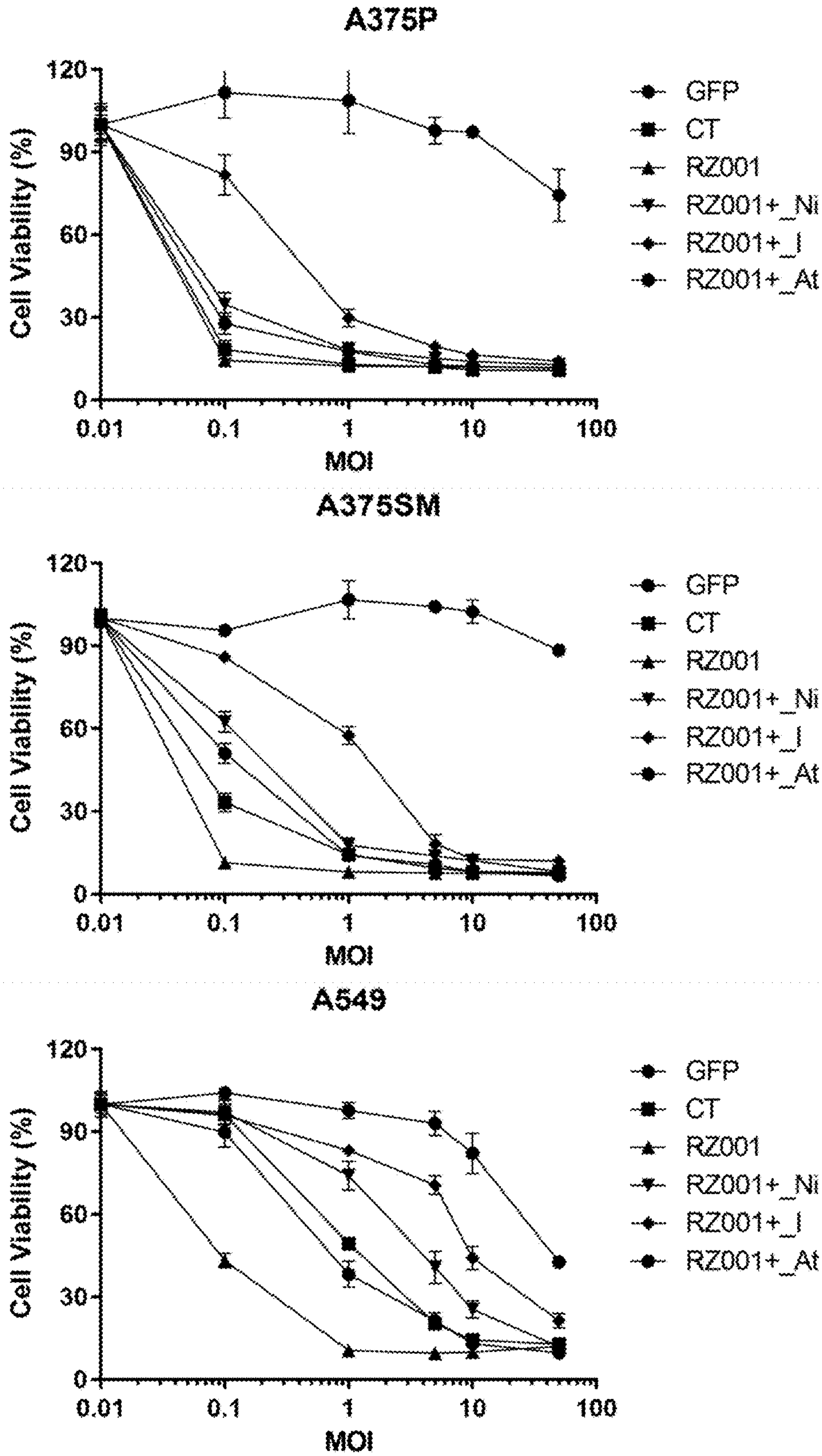
FIG. 5 illustrates a result of confirming the equivalence of RZ-001 by confirming the cell death-inducing activity of various RZ-001+ in a lung cancer cell line and a melanoma cell line.

As a result, RZ-001+ induced apoptosis of melanoma cells and lung cancer cells, and at 1 MOI or higher, RZ-001+ except RZ-001+PD1(I) had a cell death-inducing activity at a similar level to RZ-001 (FIG. 5).

Embodiment 3: Preparation of Stable Cell Line Expressing Immune Checkpoint Inhibitor 3-1. Preparation of Stable Cell Line Before confirming an effect of the vector prepared in Embodiment 1, a stable cell line expressing an immune checkpoint inhibitor was prepared as follows.

$2\times10^5$ cells of 293A cells were dispensed in a 35 mm culture dish, and then incubated for 24 hours in a 37° C. 5% $CO_2$ incubator. Then, 1 μg of each immune checkpoint inhibitor expression vector and 100 μl of Opti-MEM were put into a 1.5 ml tube and mixed, and 5 μl of Lipofectamine 2000 and 100 μl of a serum-free medium were put into another 1.5 ml tube, mixed, and then left at room temperature for 5 minutes. Thereafter, the contents of the two tubes were mixed and stored at room temperature for minutes to form a liposome-type complex. After 20 minutes, the tube was centrifuged for 10 seconds, sprayed on each cell, transfected, and changed to a new medium after 4 hours. The cells were incubated for 24 hours in a 37° C. 5% $CO_2$ incubator and then washed with 1×PBS, treated with trypsin to be detached, and then transferred to a 100 mm culture dish and incubated. Every 2 to 3 days, the medium was replaced with a medium containing an antibiotic geneticin (G418) at a concentration of 5 μg/ml. Cell clones were selected and grown, and then the expression of the immune checkpoint inhibitor was confirmed.

Proteins were isolated from a cell supernatant to perform Western blotting, RNA was extracted from the cells, and the expression level of the immune checkpoint inhibitor was confirmed by RT-PCR.

3-2. Confirmation of Expression and Affinity of Immune Checkpoint Inhibitor

The stable cell line prepared in 3-1 above was incubated, and then proteins were isolated from the cell supernatant to perform Western blotting, and RNA was extracted from the cells to confirm the expression of an immune checkpoint inhibitor by RT-PCR.

Figure 6A:
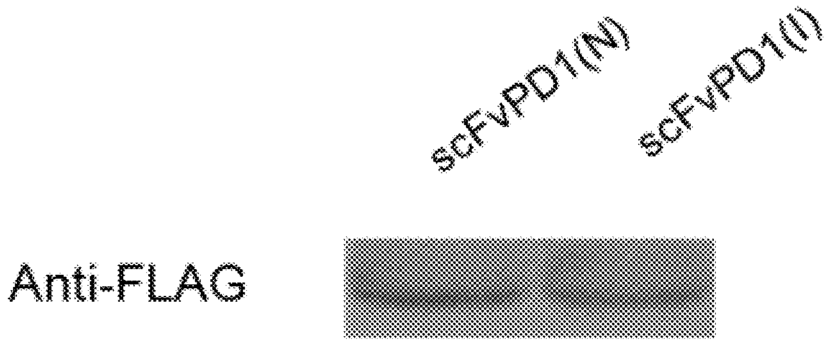
FIGS. 6A and 6B illustrate a result of confirming the expression level of an immune checkpoint inhibitor after preparing a stable cell line for expressing scFvPD1 (N) or scFvPD1 (I), which is an immune checkpoint inhibitor.
Figure 6B:
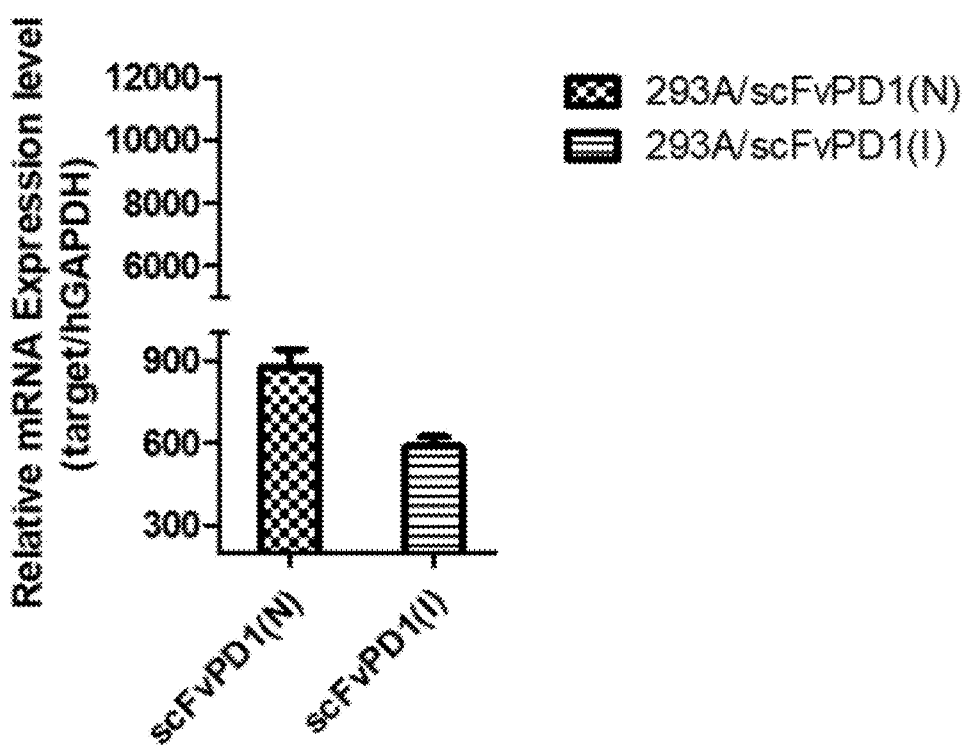

As a result, it was confirmed that all immune checkpoint inhibitors introduced into 293A cells were expressed well (FIG. 6A), and as a result of confirming the mRNA level, it was confirmed that the immune checkpoint inhibitors were well expressed (FIG. 6B).

3-3. Confirmation of Affinity of Expressed scFvPD1

Figure 7A:
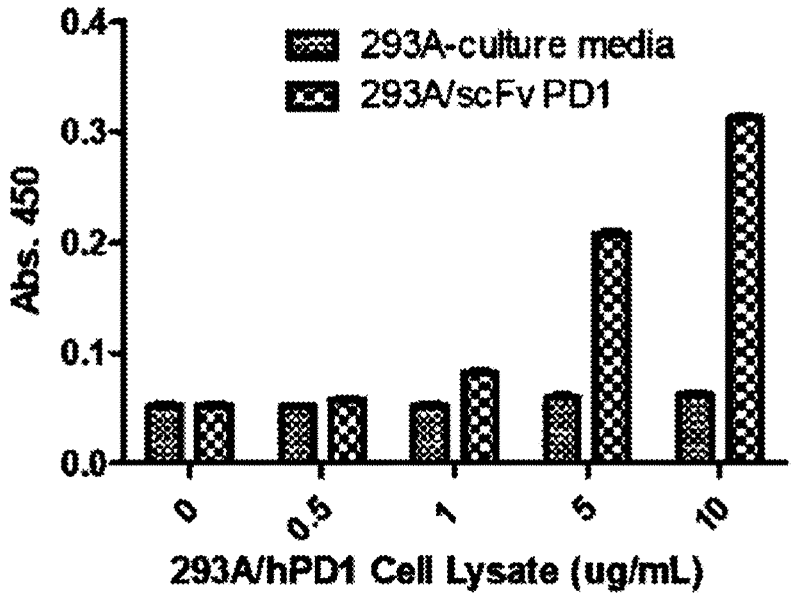
FIGS. 7A and 7B illustrate a result of reacting cell lysates expressing human PD1 (hPD1) or mouse PD1 (mPD1) with scFvPD1 recovered from a stable cell line for expressing scFvPD1.
Figure 7B:
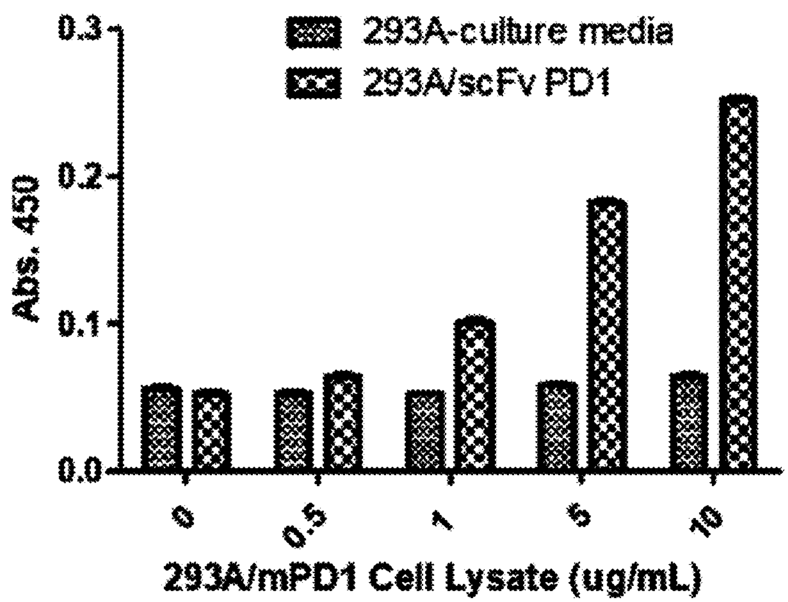

Cells expressing human PD1 (hPD1) or mouse PD1 (mPD1) were incubated to prepare a cell lysate, which was attached to a 96-well plate. Then, the cell lysate was reacted with scFvPD1 (I) recovered from the stable cell line culture medium of 2-1 above, and the antibody affinity was confirmed by an ELISA method. As a control, a 293A cell culture medium was used. As a result, it was confirmed that the absorbance increased as the concentration of the cell lysate increased, and then it could be seen that scFvPD1(I) functioned well as an antibody (FIG. 7).

3-4. Preparation of Mouse PDL1 Expression Stable Cell Line

Figure 8A:
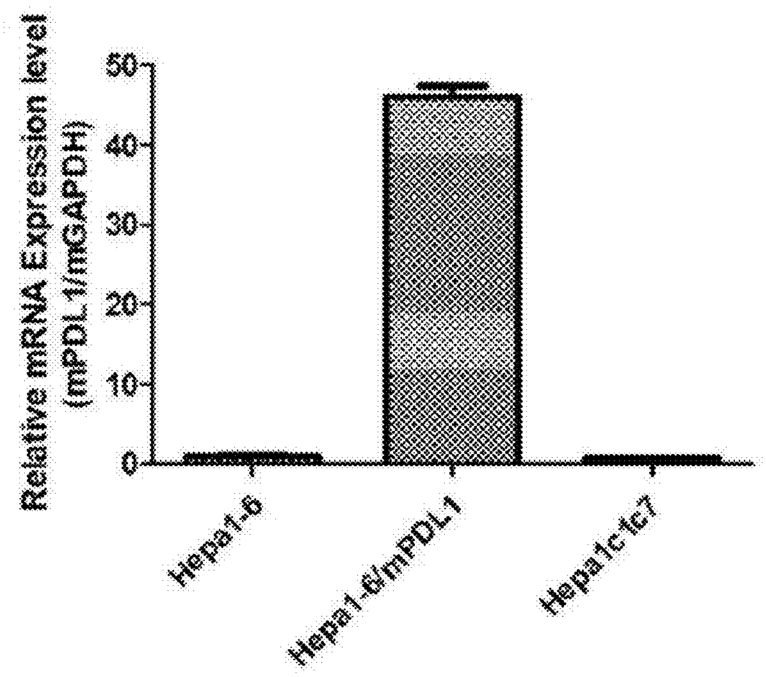
FIGS. 8A-8C illustrate a result of confirming the expression of mPD1 after preparing a stable cell line for expressing mouse PD1 (mPD1) using Hepa1-6 cells, which is a mouse liver cancer cell line.
Figure 8B:
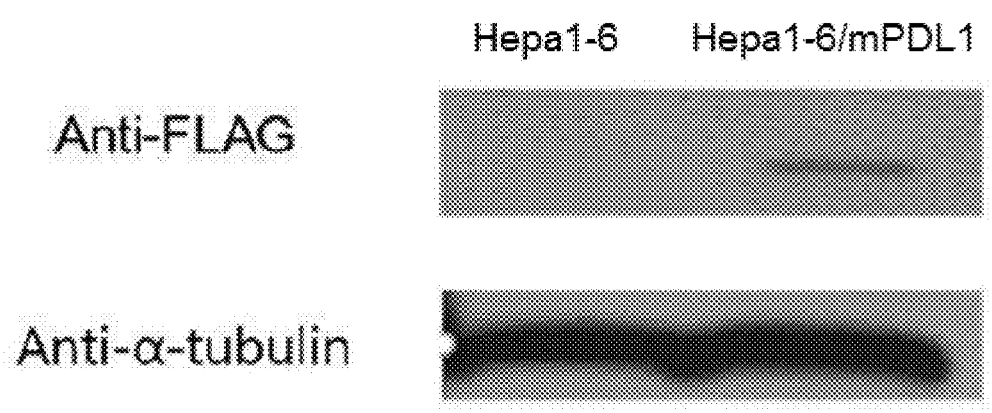
Figure 8C:
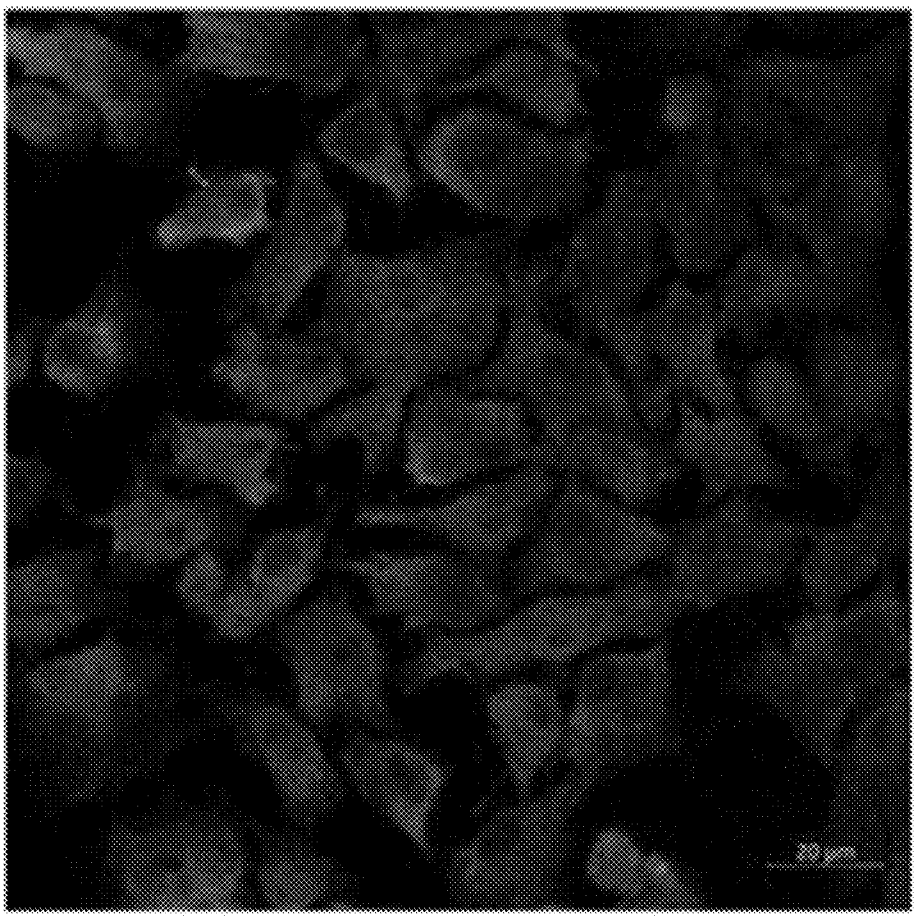

In order to confirm a combined effect of co-expression of a cancer therapeutic gene and an immune checkpoint inhibitor, a stable cell line expressing mouse PDL1 (mPDL1) was prepared in the same manner as in Embodiment 3-1. Briefly, mPDL1/pCMV6 was introduced into a mouse-derived liver cancer cell line, Hepa1-6 cell line and treated with geneticin, and cell clones were selected for 3 weeks. As a result of confirming the expression level of mPDL1 by incubating the selected cell clones, it was confirmed that mPDL1 was expressed at a high level compared to other mouse liver cancer cell lines Hepa1-6 and Hepa1c1c7 (FIG. 8).

Hereinafter, the Hepa1-6 stable cell line into which mPDL1 has been introduced was referred to as Hepa1-6/mPDL1.

Embodiment 4. Confirmation of Effect of RZ-001+ Expression Vector in Hepa1-6 Stable Cell Line 4-1. Infection Test A Hepa1-6 or Hepa1-6/mPDL1 cell line was treated with mRZ-001+ prepared in Embodiment 1 at a concentration of 10 MOI.

The used vectors were as follows:

mCRT-122T (CMV promoter+mTERT ribozyme+HSVtk+miR-122T(3X)), mCRT-122T/scFvPD1(I) (CMV promoter+mTERT ribozyme+HSVtk+scFvPD1(I)+miR-122T(3X)), After 24 hours of virus treatment, genomic DNA was extracted from the cells, and the degree of virus infection was confirmed by performing RT-PCR targeting E4.

Figure 9:
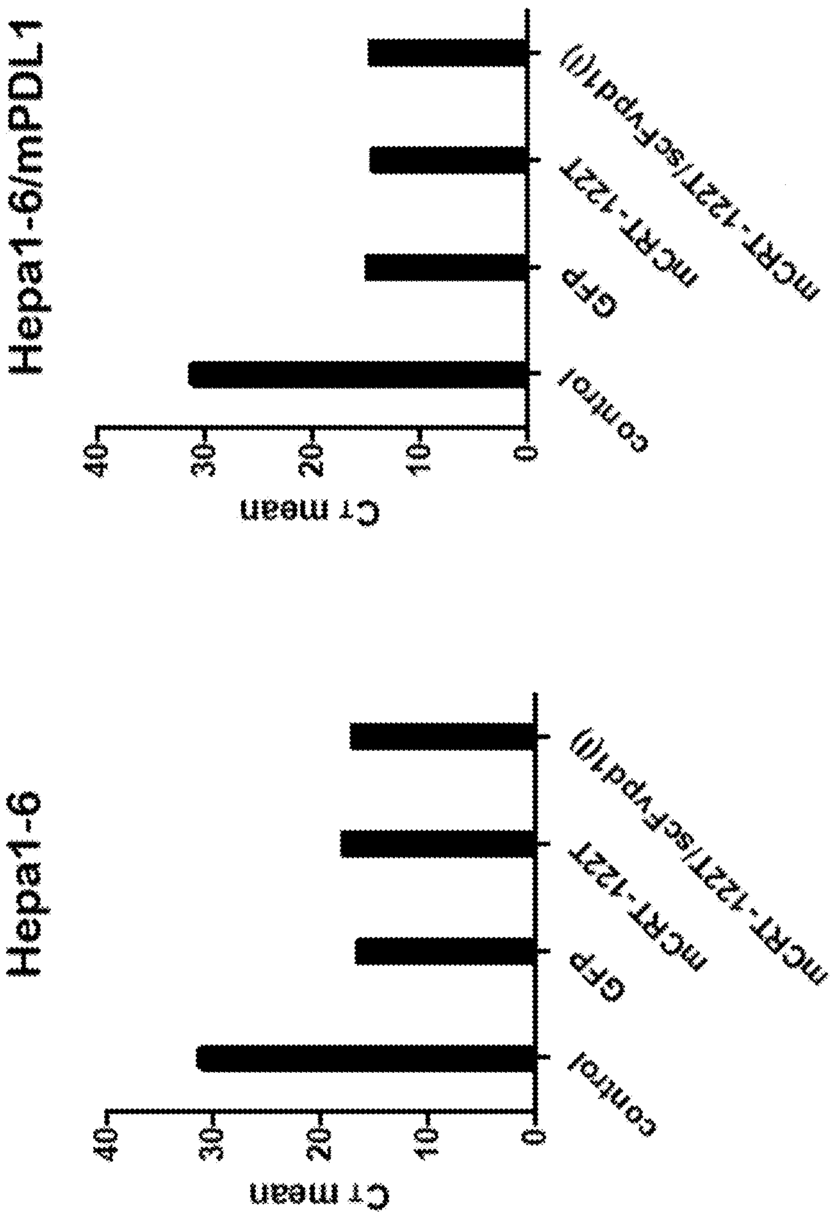
FIG. 9 illustrates a result of confirming the degree of virus infection after treating Hepa1-6 cells and Hepa1-6 cells (Hepa1-6/mPD1) expressing mouse PD1 (mPD1) with mRZ-001+, respectively. The mRZ-001+ is a virus vector capable of expressing a cancer therapeutic gene (HSVtk) and an immune checkpoint inhibitor (ICI) in a cancer-specific manner and expressing a mouse TERT target trans-splicing ribozyme with a complementary sequence (mir-T) to miR-122a at a 3'-terminal.

As a result, it was confirmed that the average Ct values of E4 appeared at a similar level in each experimental group (FIG. 9).

4-2. Confirmation of Cell Viability

Hepa1-6, Hepa1-6/mPDL1, and Hepa1cic7 cells were dispensed at $1\times10^4$ cells in a 96-well, respectively, and then treated with adenovirus containing the mRZ-001+ expression vector prepared in Embodiment 1 at different MOIs. After 24 hours of the adenovirus treatment, ganciclovir (GCV) was diluted in a cell culture medium to a final concentration of 100 μM and then added to each well. GCV was treated a total of three times at 2-day intervals, and after 24 hours of the last GCV treatment, an MTS assay reagent was added and then absorbance was measured at a wavelength of 450 nm to confirm cell viability.

Figure 10:
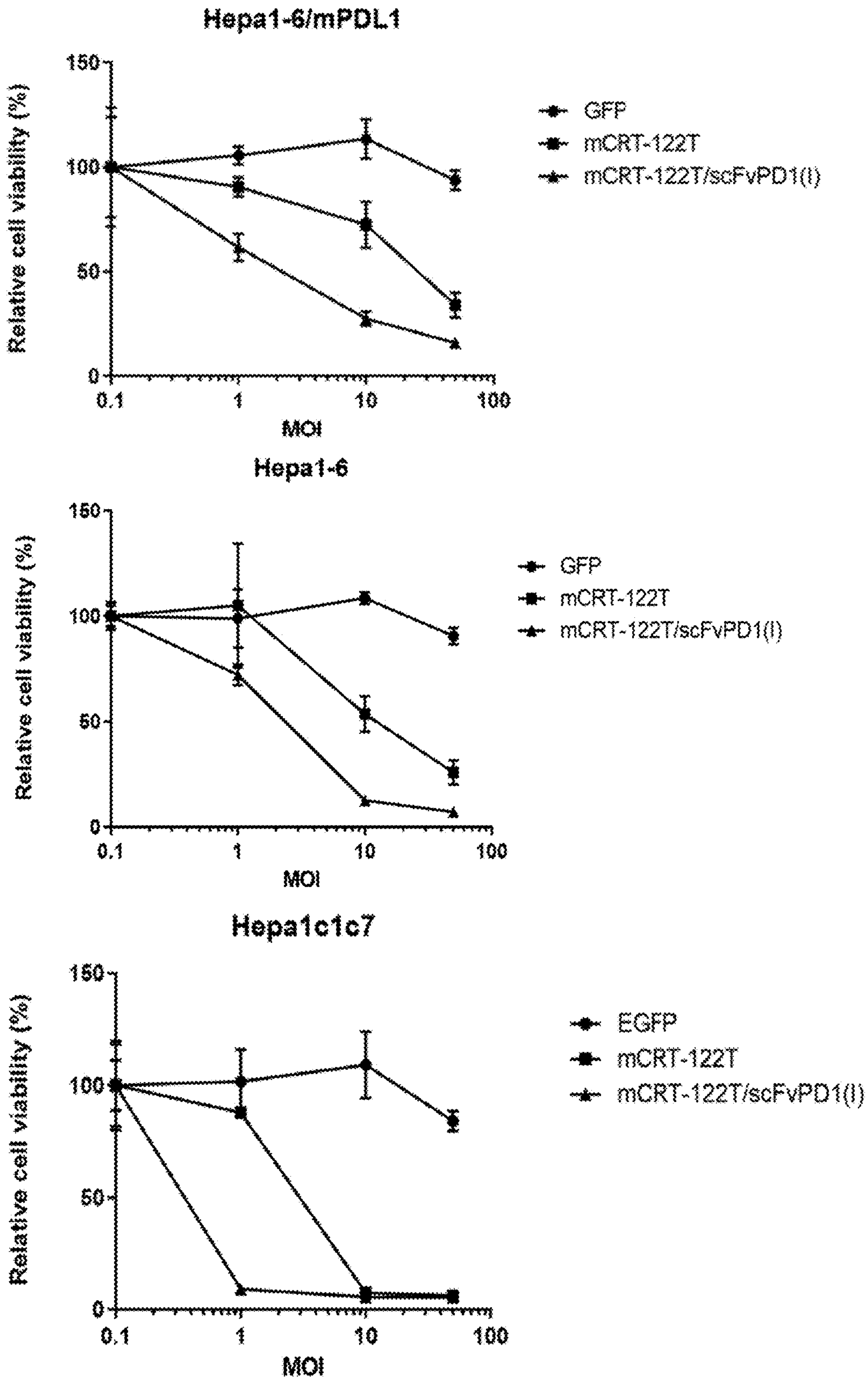
FIG. 10 illustrates a result of confirming cell viability after treating Hepa1-6, Hepa1-6/mPD1, and Hepa1cic7 cells with mRZ-001+, respectively.

As a result, it could be seen that apoptosis increased in an experimental group treated with a ribozyme expression vector compared to a control group (EGFP), and particularly, it was confirmed that compared to an mCRT-122T-treated group, the apoptosis level was significantly high in an immune checkpoint inhibitor expression vector-treated group (mCRT-122T/scFvPD1 (I)) (FIG. 10).

4-3. Comparison of Expression of PD1 or PDL1 Antibody

Hepa1-6, Hepa1-6/mPDL1, and Hepa1c1c7 cells were treated with adenovirus containing an immune checkpoint inhibitor expression vector at 50 MOI, and after 24 hours, proteins were isolated from cells to confirm the expression level of the immune checkpoint inhibitor. The expected size of the protein was about 28 kDa including a signal peptide.

Figure 11:
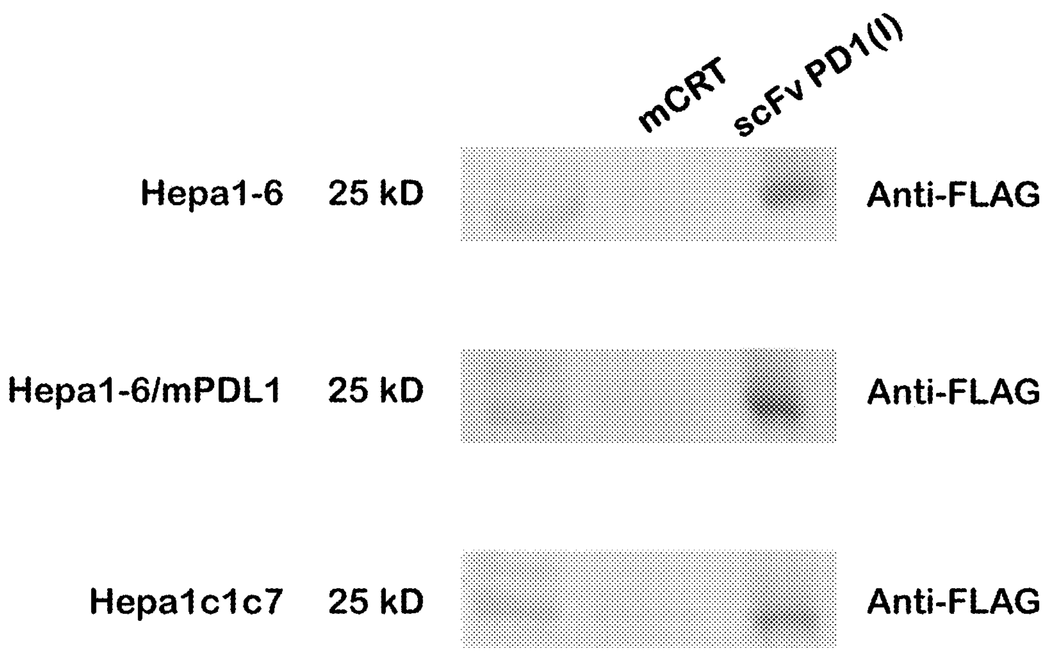
FIG. 11 illustrates a result of confirming the expression level of an immune checkpoint inhibitor after treating Hepa1-6, Hepa1-6/mPD1, and Hepa1cic7 cells with mRZ-001+, respectively.

As a result of confirmation, the immune checkpoint inhibitor was expressed in all three types of cell lines (FIG. 11).

4-4. Apoptotic Efficacy

Hepa1-6 and Hepa1-6/mPDL1 cells were dispensed in $2\times10^5$ cells in a 6-well plate, respectively, and treated with adenovirus containing an mRZ-001+ expression vector at 5 MOI. After 24 hours of the virus treatment, GCV was diluted in a cell culture medium to a final concentration of 100 μM and then added to each well. After further incubation for 24 hours, each well was treated with propidium iodide (PI), and the degree of apoptosis was analyzed by flow cytometry.

Figure 12:
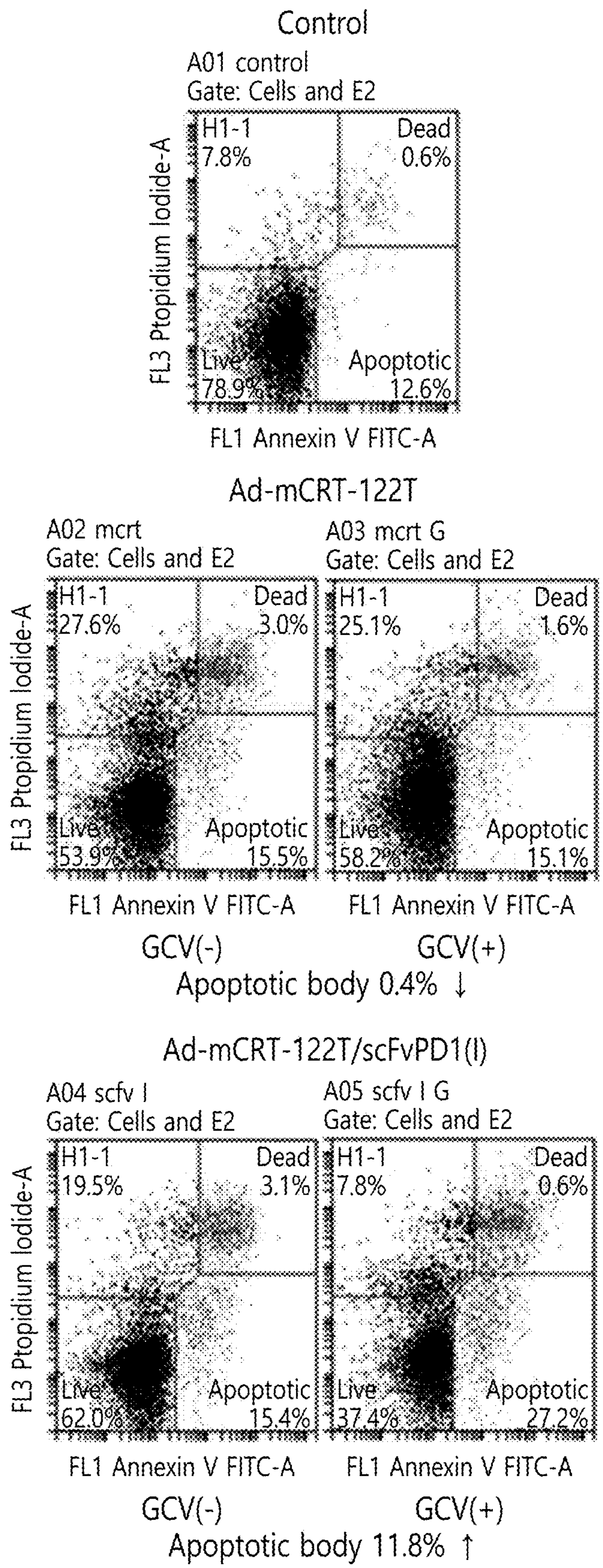
FIG. 12 illustrates a result of confirming the apoptosis level by flow cytometry after treating Hepa1-6 cells with mRZ-001+.
Figure 13:
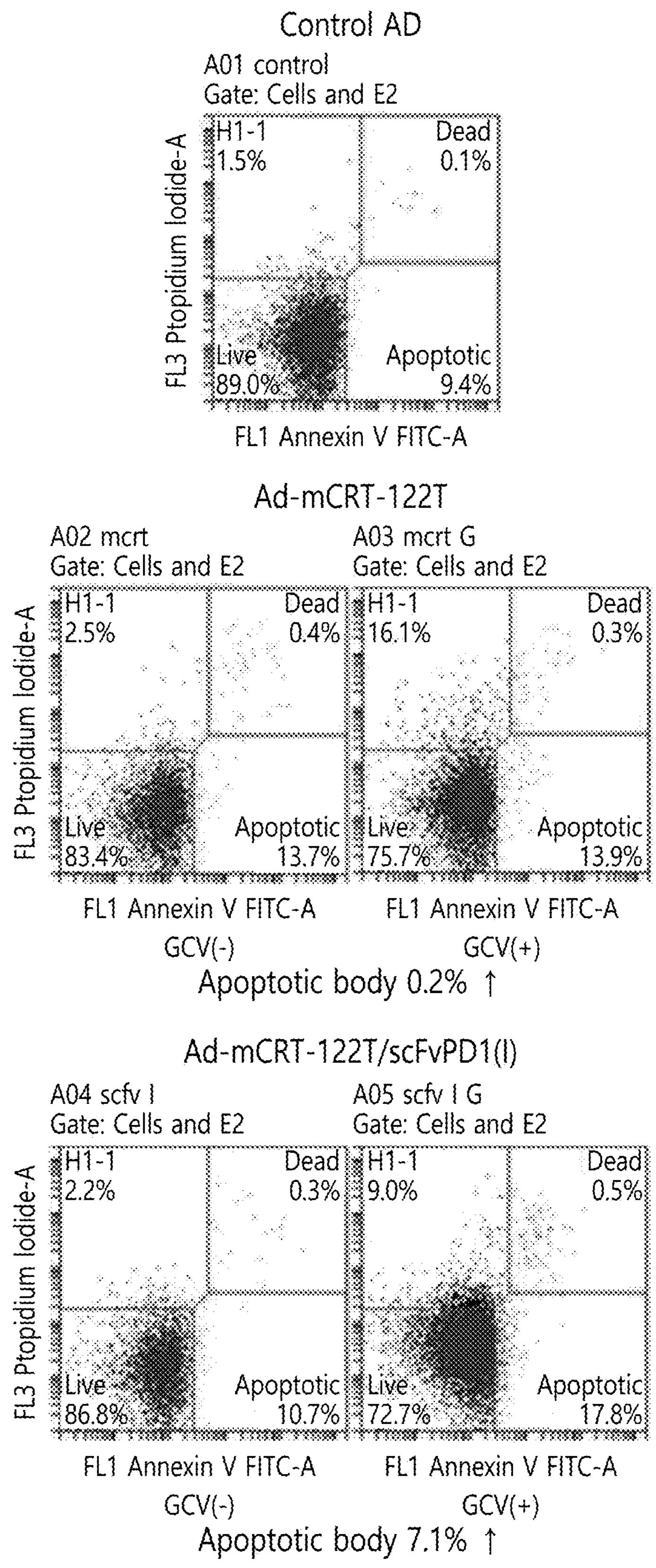
FIG. 13 illustrates a result of confirming the apoptosis level by flow cytometry after treating Hepa1-6/mPDL1 cells with mRZ-001+.

As a result of the analysis, both Hepa1-6 and Hepa1-6/mPDL1 cells showed little change in the level of early apoptosis by GCV treatment in an mCRT-122T vector-treated group, but in an immune checkpoint inhibitor expression vector-treated group, it was found that early apoptosis significantly increased after GCV treatment (FIGS. 12 and 13).

Embodiment 5. Introduction of RZ-001+ Expression Vector in Human Liver Cancer Cell Line Confirmation of Release of Immune Checkpoint Inhibitor According to Introduction of RZ-001+

Human liver cancer cell lines, Hep3b and SNU398 cells, were dispensed at 1×6 cells in a 607t culture dish, and on the next day, the used medium was exchanged with a 2% FBS medium, and adenovirus containing the RZ-001+ expression vector was treated at 30 MOI. At 48 hours after the virus treatment, the medium was placed in a 15 ml tube and centrifuged at 1,500 rpm for 5 minutes to remove cell debris. Each sample was transferred to a 10 k centricon and concentrated at 3,000 rpm for 15 to 30 minutes so that the total volume of the samples was 500 μl. The concentrated samples were prepared to using a 5× sample buffer and denaturation was induced at 100° C. for 5 minutes. The prepared samples were loaded in 40 μl each on 12% SDS-PAGE. Each cell was washed with PBS and harvested, added and treated with a RIPA buffer at 4° C. for 20 minutes, and then centrifuged at 13,000 rpm for 10 minutes to obtain a supernatant, and the supernatant was transferred to a new tube and quantified by BCA quantification. The samples were prepared so that the quantified proteins were 30 μg/well and loaded on SDS-PAGE in the same manner as above. After PAGE isolation, the PAGE was transferred to PVDF, blocked in 5% skim milk in PBS-T for 30 minutes, and anti-FLAG was diluted 1:1,000 and reacted 0/N at 4° C. On the next day, after washing with PBS-T, a secondary antibody anti-mouse/HRP was diluted 1:2,000 and reacted for 1 hour, and then the expression level was detected with an ECL solution.

Figure 14:
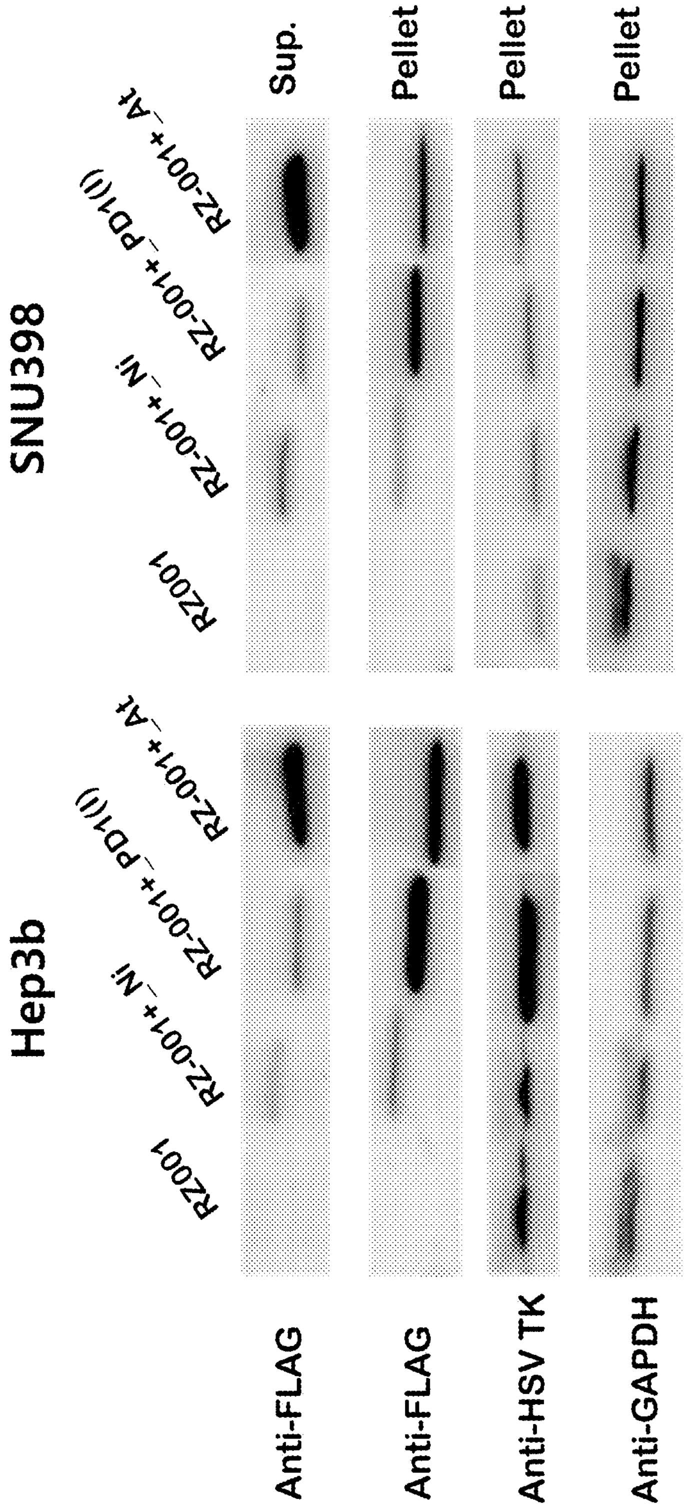
FIG. 14 illustrates a result of measuring the expression levels of target genes HSVtk and scFv in Hep3b and SNU398 cells after treatment with RZ-001+.

As a result, it was confirmed that scFv was released from the liver cancer cell line treated with RZ-001+. In particular, the highest level of scFv release was confirmed in RZ-001+ PDL1(At). From the above, it can be seen that the cells into which the RZ-001+ expression vector was introduced actively release scFv, and that RZ-001+ may be applied to cancer cells (FIG. 14).

5-2. Confirmation of Trans-Splicing Reaction According to Introduction of RZ-001+

It was confirmed whether RZ-001+ effectively trans-spliced a targeting TERT mRNA in liver cancer cell line treated with an adenovirus in Embodiment 5-1. Cells treated with 30 MOI virus in Embodiment 5-1 were quantified by preparing RNA using TRIzol after 48 hours of virus treatment. Using an RT kit (Genet bio #SR3000), 3 μg of RNA and 1 μL of RT primer were mixed and reacted (50° C. 60 min, 70° C. 10 min). PCR was performed using a primer premix (Bionia, #k-2611) shown in Table 1 below, and 40 cycles of the PCR were performed under the conditions of 95° C. 30 sec, 59° C. 30 sec, and 72° C. 30 sec. Subsequently, the amplified product was subjected to electrophoresis on a 2% agarose gel to confirm a band of a target size. Cloning was performed using a TA vector through gel elution of the target size band and sequencing was performed.

TABLE 1

| | |
|---|---|
| RT primer (HSV-tk) | 5'-agttagcctcccccatctc-3' (SEQ ID NO: 8) |
| hTERT | 5'-GGAATTCGCAGCGCTGCGTCCTGCT-3' (SEQ ID NO: 9) |
| HSVtk | 5'-GTGAGGACCGTCTATATAAACCCGCAGTAG-3' (SEQ ID NO: 10) |

Figure 15:
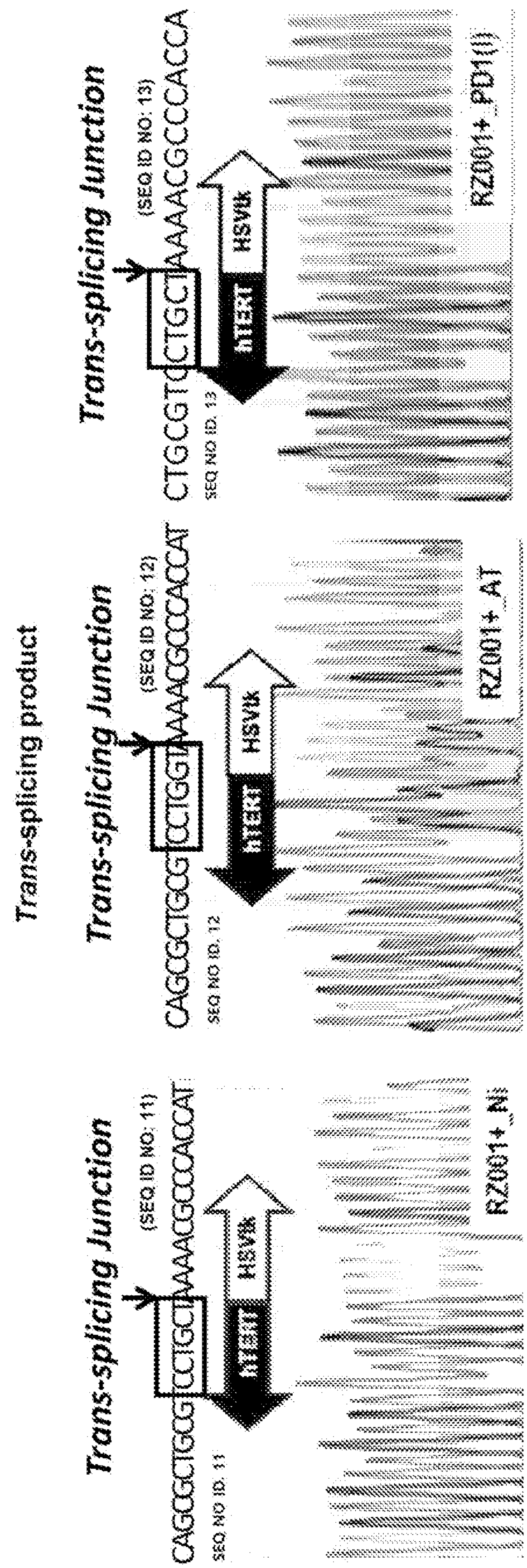
FIG. 15 illustrates a result of confirming whether trans-splicing has occurred to target TERT mRNA by a ribozyme expressed in a liver cancer cell line treated with RZ-001+ and a location of the trans-splicing.

As a result, in the liver cancer cell line sample treated with RZ-001+, a band of a product size that may be produced when trans-splicing occurred was confirmed, and it was confirmed that a product nucleotide sequence of the band was trans-spliced at a target site of a target RNA. From the above, it can be seen that RZ-001+ may induce a trans-splicing reaction by accurately reacting to the target RNA and the target site in the introduced liver cancer cells (FIG. 15).

5-3. Confirmation of Bioactivity of Released Immune Checkpoint Inhibitor

Subsequently, a PD1/PDL1 blockade bioassay (Promega, #J1250) was performed to confirm whether an immune checkpoint inhibitor released by an RZ-001+-introduced liver cancer cell line could effectively bind to an immune checkpoint protein to block a signal thereof. In the PD1/PDL1 blockade bioassay, when PD-1 on the surface of PD-1 effector cells bound to PDL1 present on APC cells or cancer cells under a condition without a PD-1 or PDL-1 cancer immunotherapy agent, the PD1/PDL1 interaction suppressed TCR-mediated luminescence so that a luciferase signal was not detected. However, under the condition with the cancer immunotherapy agent, a system was used in which the binding of PDL1 and PD1 was hindered by the binding of the cancer immunotherapy agent, and the TCR was activated, and luciferase gene expression was induced through the activation of an NFAT signal so that a luciferase signal was increased. The experiment was performed according to a manufacturer's recommended protocol. Specifically, PDL1 aAPC/CHO-K1 cells were prepared on a white plate. On the next day, the medium of the cells was removed, 40 μl of the concentrated sample of Embodiment 3-1 was loaded on the plate, and PD-1 effector cells were prepared on the plate loaded with the concentrated sample, and a reaction was induced at 37° C. for 6 hours. Subsequently, the cells were added with a bio-Glo reagent and incubated for 5 to 10 minutes at room temperature, and then fluorescence was measured using a luminometer.

Figure 16:
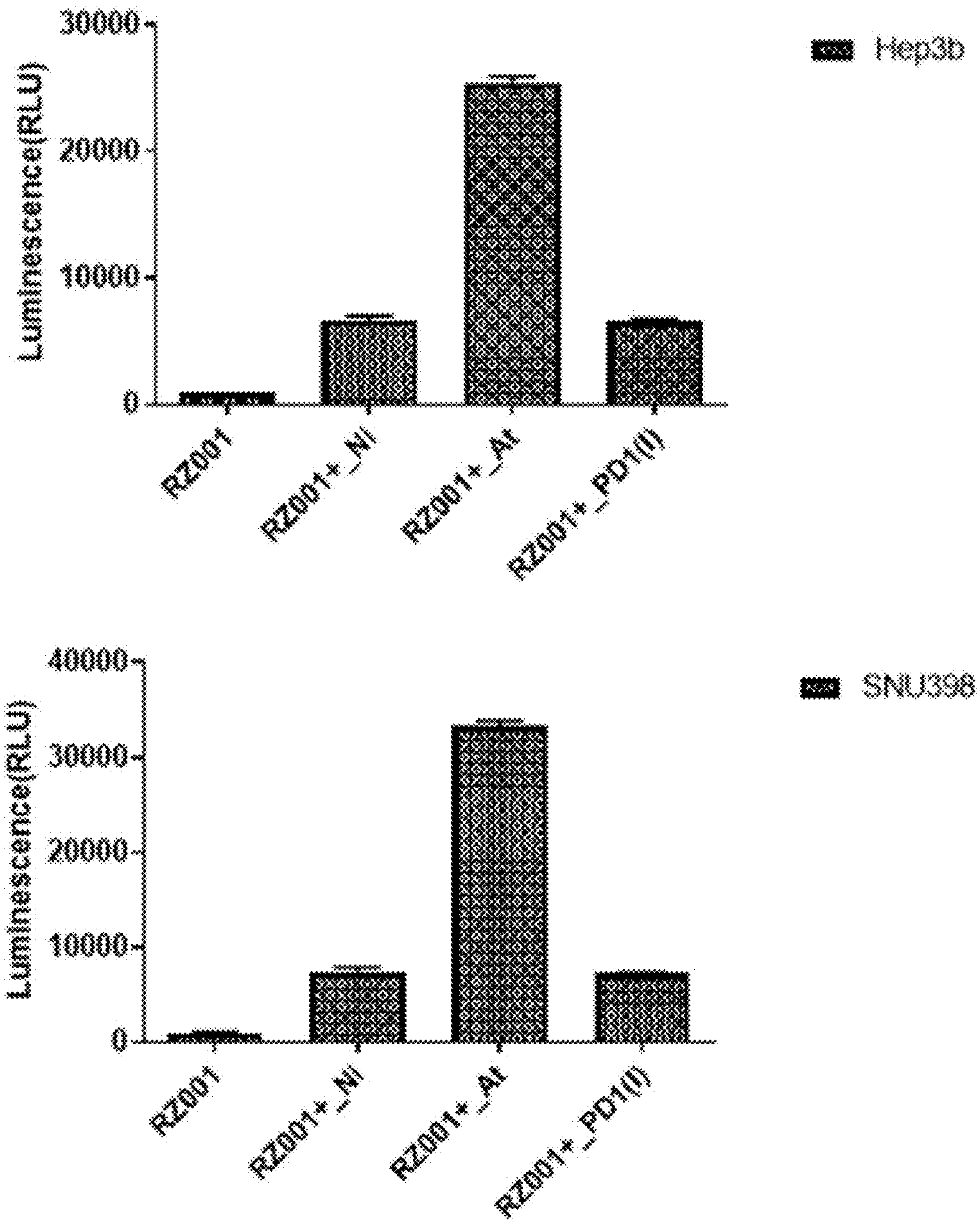
FIG. 16 illustrates a result of treating Hep3b and SNU398 cells with RZ-001+ and performing PD1/PDL1 blockade bioassay.

As a result of measuring the activity of the cancer immunotherapy agent released using the culture medium of the liver cancer cell line sample treated with RZ-001+, an increase in bioactivity was confirmed in all cells treated with RZ-001+, and from the above, it can be seen that the immune checkpoint inhibitor is produced and released within cells by RZ-001+ virus infection. In particular, in response to the results of Embodiment 5-1, the bioactivity increased the most in the case of RZ-001+ At, so that the most cancer immunotherapy agent was produced and released, and it can be seen that the released cancer immunotherapy agent has excellent activity. (FIG. 16).

Embodiment 6. Introduction of RZ-001+ Expression Vector in Human Brain Tumor Cell Line 6-1. Confirmation of PD-L1 Expression in RZ-001+-Introduced Cell Line A human liver cancer cell line SNU398 and a human brain tumor cell line U87MG were dispensed into a 12-well plate at $5\times10^4$ cells/well/1 mL and incubated for 2 days. Cells are lysed using a RIPA buffer to extract a total protein. The extracted total protein was quantified by a BCA quantification method, all samples were prepared to have the same amount of protein, the prepared protein sample was loaded on SDS-PAGE, transferred to PVDF, and then the antigen-antibody reaction was performed in 5% skim milk in TBS-T and the expression level of a target protein was measured.

Figure 17:
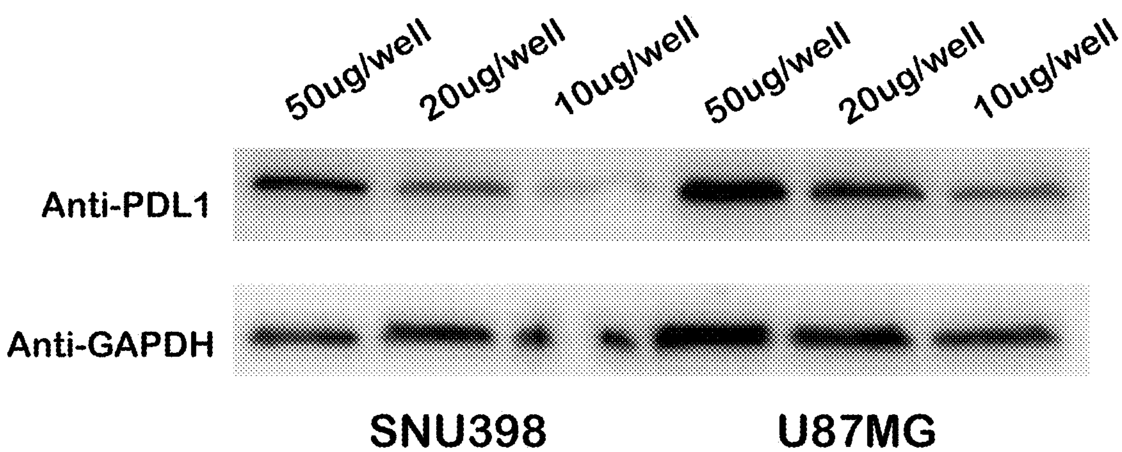
FIG. 17 illustrates a result of confirming the expression of PD-L1 in each cell of SNU398, a human liver cancer cell line, and U87MG, a human brain tumor cell line.

As a result, by confirming the expression of a PD-L1 protein in both the liver cancer cell line SNU398 and the brain tumor cell line U87MG, the effectiveness may be presented by application of RZ-001+ PDL1 expressing the immune checkpoint inhibitor to the liver cancer and the brain cancer (FIG. 17).

6-2. Confirmation of Release of Immune Checkpoint Inhibitor According to Introduction of RZ-001+

In the same manner as in Embodiment 5-1, the release of scFv was confirmed from an adenovirus-infected brain tumor cell line containing an RZ-001+ expression vector. An experimental method was performed in the same manner as in Embodiment 5-1 with only the virus treatment concentrations of 10 MOI and 20 MOI.

Figure 18:
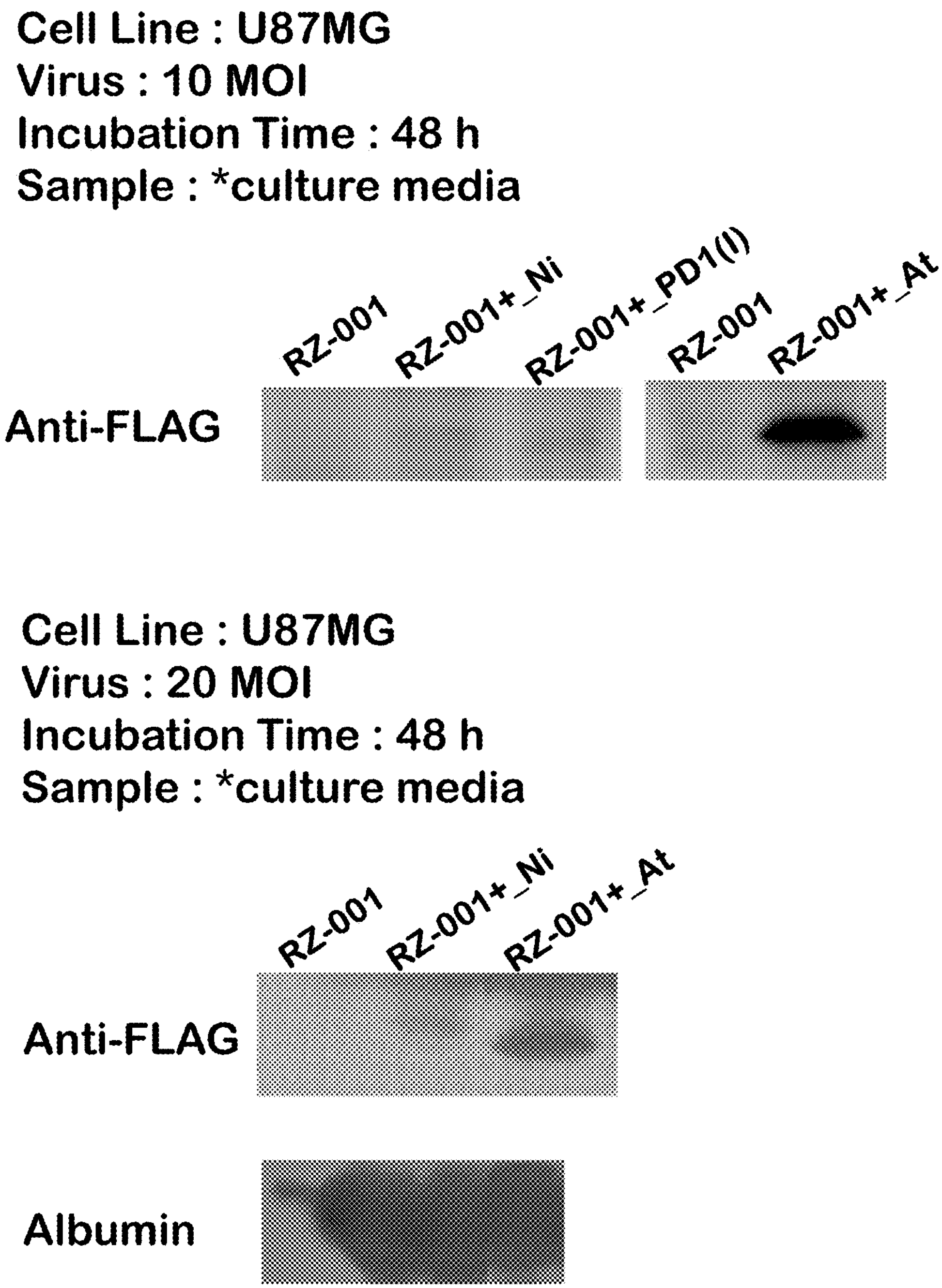
FIG. 18 illustrates a result of confirming the expression level of an immune checkpoint inhibitor in U87MG cells treated with RZ-001+ at a concentration of 10 MOI or 20 MOI.

As a result, even in a Glioblastoma cell line, U87MG, the release of scFv was confirmed in cells according to the introduction of the RZ-001+ expression vector, and in particular, the most release amount of scFv was confirmed in cells introduced with the RZ-001+ At expression vector (FIG. 18).

6-3. Confirmation of Bioactivity of Released Immune Checkpoint Inhibitor

Next, a supernatant of the cells treated with the virus containing the RZ-001+ PDL1(At) expression vector was isolated and a PD1/PDL1 blockade bioassay (Promega, #J1250) was performed in the same manner as in Embodiment 5-3. As a control, commercially available Atezolizumab was used.

Figure 19:
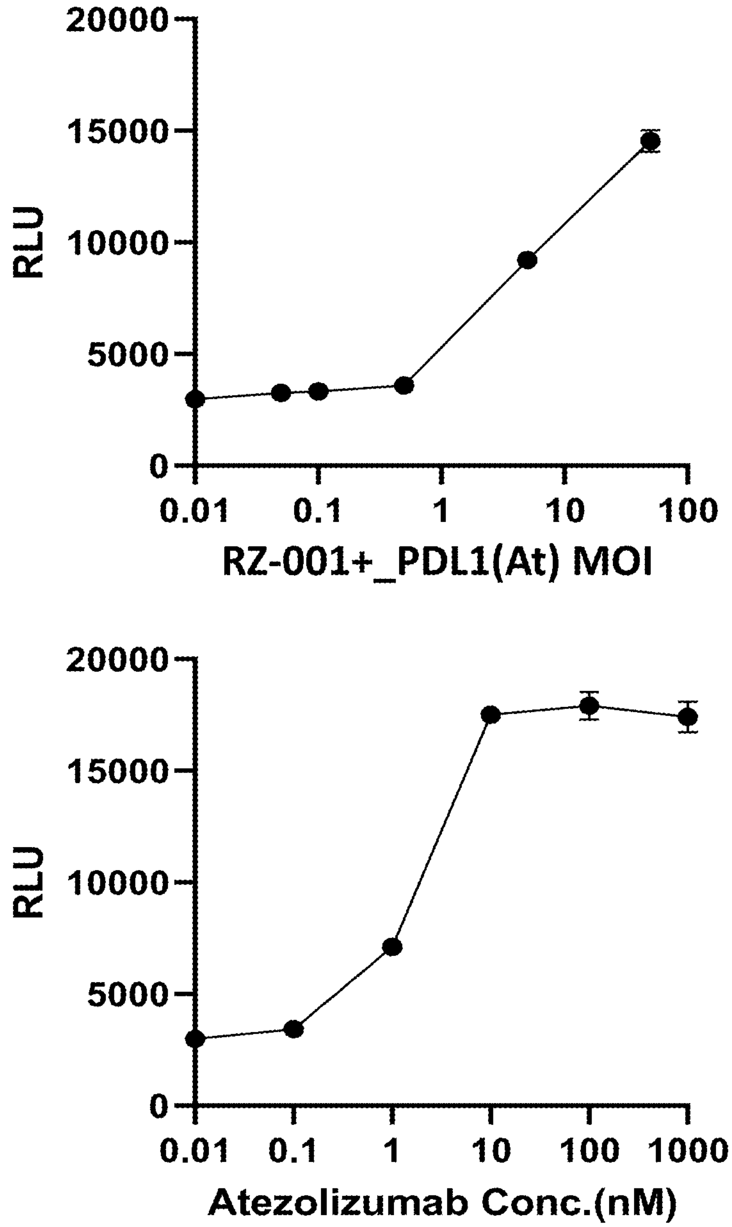
FIG. 19 illustrates a result of treating U87MG cells with increasing amounts of RZ-001+ and performing PD1/PDL1 blockade bioassay. As a control, PD1/PDL1 blockade bioassay was performed with Atezolizumab (anti-PDL1).

As a result, it was confirmed that the luciferase activity increased as the concentrated sample obtained from the cells treated with the virus at a high MOI was treated (FIG. 19).

Embodiment 7. Confirmation of Anticancer Effect of RZ-001+ In Vivo 7-1. Confirmation of Effect of RZ-001+ in PBMC-Humanized Liver Cancer Model A mouse xenograft subcutaneous model (6-week-old male NOG) mouse was injected with human PBMC 5×10 6 cells/head to prepare a PBMC-humanized mouse (PBMC-humice), and the body weight and condition of the mouse were confirmed for 7 to 10 days, 5×10 6 cells/50 μl of SNU-398 cells were subcutaneously injected and bred for 2 weeks to construct a liver cancer tumor model. Subsequently, the tumor growth and weight were measured, group separation was performed, and drug administration was performed for each group. Additionally, AST/ALT levels were measured to confirm the hepatotoxicity of the drug.

Each group was divided into a control group, an Atezolizumab (At)-administered group, an RZ-001-administered group, an RZ-001+ At-administered group, and an RZ-001 and Atezolizumab co-administered group, the virus was intratumorally administered at $1\times10^9$ VP/head twice at 48-hour intervals, and combined atezolizumab was administered intravenously three times at 2-day intervals from 2 days after virus administration at a dose of 5 mg/kg.

Figure 20A:
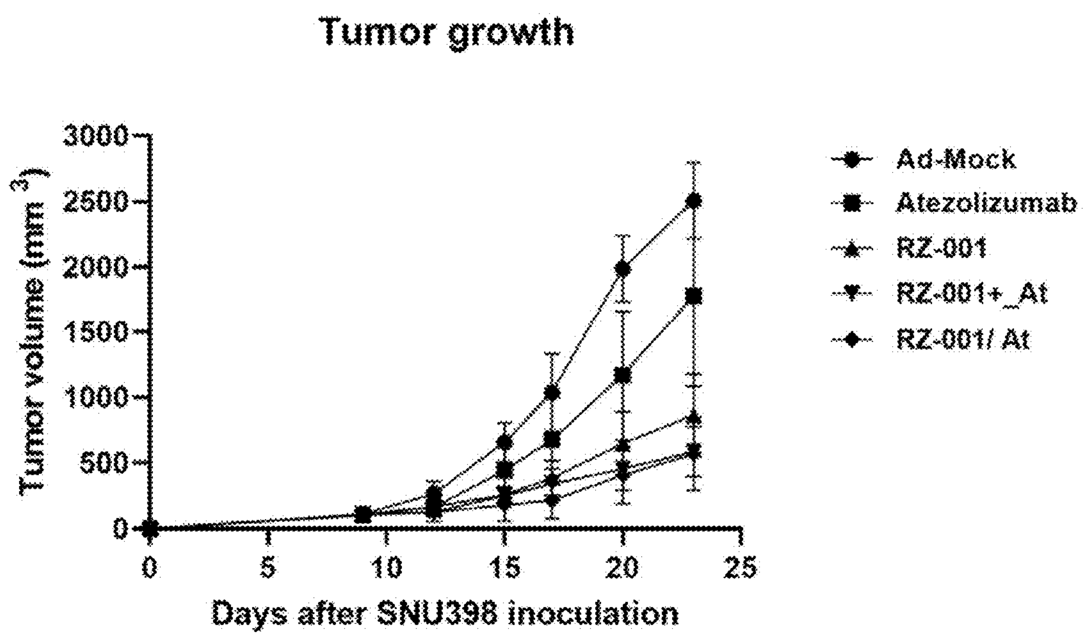
FIGS. 20A to 20C illustrate results of confirming inhibition of tumor growth and reduction of tumor weight according to RZ-001 administration, RZ-001+ At administration, or RZ-001 and At-combined administration (RZ-001/At) in a PBMC-humanized liver cancer model, and the hepatotoxicity of each administered drug, respectively.
Figure 20B:
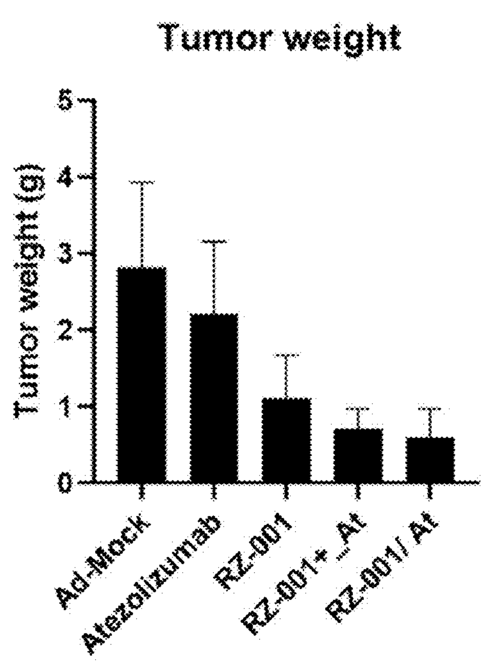
Figure 20C:
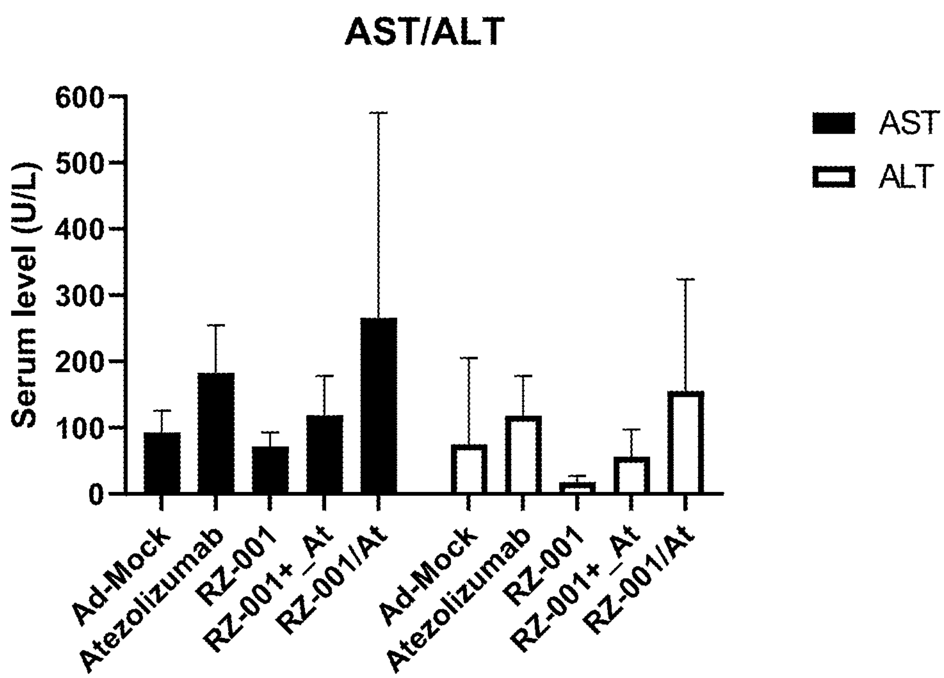

As a result, it was confirmed that the tumor volume and weight decreased when RZ-001+ At was administered compared to the single administration of RZ-001 and Atezolizumab, respectively, and it was confirmed that tumors were greatly reduced similarly to the co-administration of RZ-001 and At. Meanwhile, as a result of measuring the hepatotoxicity, the RZ-001+ At-administered group showed a decrease in AST/ALT level compared to the Atezolizumab alone or co-administered group, and showed a similar level compared to Ad-Mock, so that it can be seen that the hepatotoxicity is significantly suppressed (FIG. 20).

7-2. Confirmation of Effect of RZ-001+ in Syngeneic Orthotopic Brain Tumor Model 5-week-old male C57BL/6 mice with immunoreactivity were anesthetized, the 1 cm midline of the scalp was cut using a stereotactic tool, and then $1\times10^5$ cells/head of a mouse-derived brain cancer cell line (GL261) was transplanted to anterior 1 mm, lateral 2.3 mm, and 3 mm depth based on the bregma to prepare an Orthotopic brain tumor model. After 7 days, tumor growth was measured, group separation was performed, and drug administration was performed for each group.

Administration of the drug was performed according to the following dosage and usage.

For mRZ-001 and mRZ-001+, 3×10 9 VP/5 μL was administered directly into the tumor once.

GCV was administered at 50 mg/kg in a 100 μl liquid volume, and administered once daily from the next day after the end of virus administration, a total of 10 times.

Experimental animal groups were divided into an mRZ-001-administered group and an mRZ-001+-administered group, and a PBS-administered group was divided as a control group.

Figure 21:
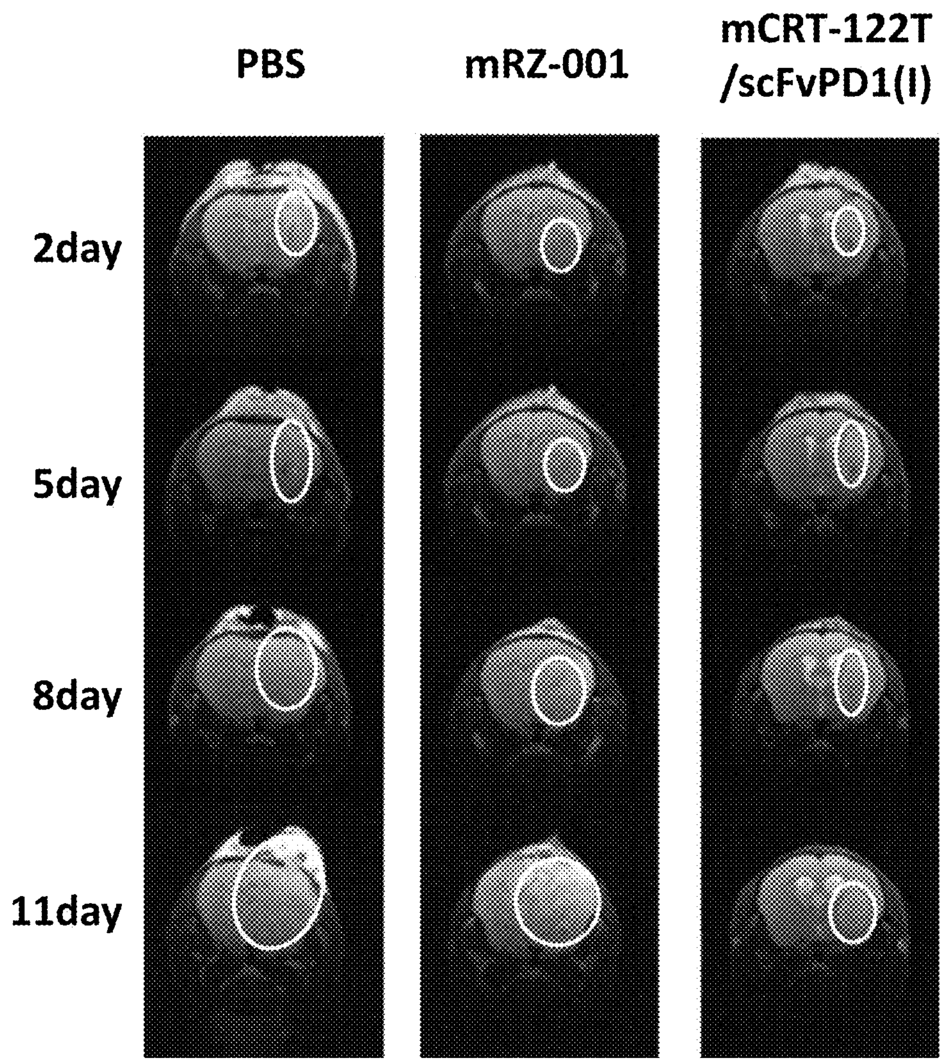
FIG. 21 shows an MRI photograph of each drug-administrated group in an Orthotopic brain tumor syngeneic model.

In order to measure the tumor volume, MRI imaging was performed every 3 days, including the next day after drug administration, and five slices were selected based on a tumor implantation location, and tumor region of interest (ROI) analysis over time was performed using an ImageJ system (FIG. 21). Specifically, a Biospec 47/40 USR (Bruker, Ettlingen, Germany) horizontal bore magnet was used for MRI imaging. During imaging, while the animal was anesthetized, respiratory rate, heart rate, and body temperature were observed using an animal monitoring-gating system during image acquisition, and a warm bed was used to maintain a body temperature. Images to confirm tumor growth and growth inhibition were taken at 15 consecutive axial slices using an RARE sequence, and the related conditions were as follows:

repetition time (TR)=2200 ms
echo time (TE)=40 ms
slice thickness=0.75 mm
matrix=192×192
flip angle (FA)=90
field of view (FOV)=18×18 mm 2
average=4
echo train length (ETL)=8.

Figure 22:
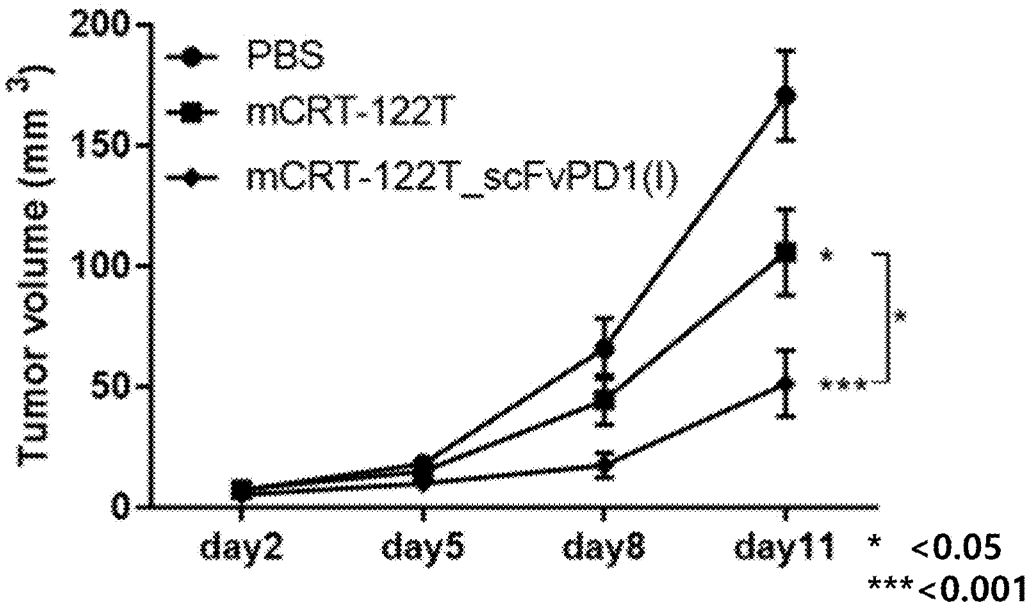
FIG. 22 illustrates a result confirmed by comparing the reduction degree of tumor volume according to mRZ-001 administration and mRZ-001+ administration in an Orthotopic brain tumor syngeneic model.

The tumor volume was a result of setting the next day as Day 1 based on mRZ-001 and treating total 10 times up to Day10 together with GCV treatment, and the reduced degree of the tumor volume was confirmed as compared with a PBS-administered group. As a result, the tumor volume decreased according to the virus infection, and the administration of mRZ-001+ reduced the tumor volume more significantly than the administration of mRZ-001 (FIG. 22).

Figure 23:
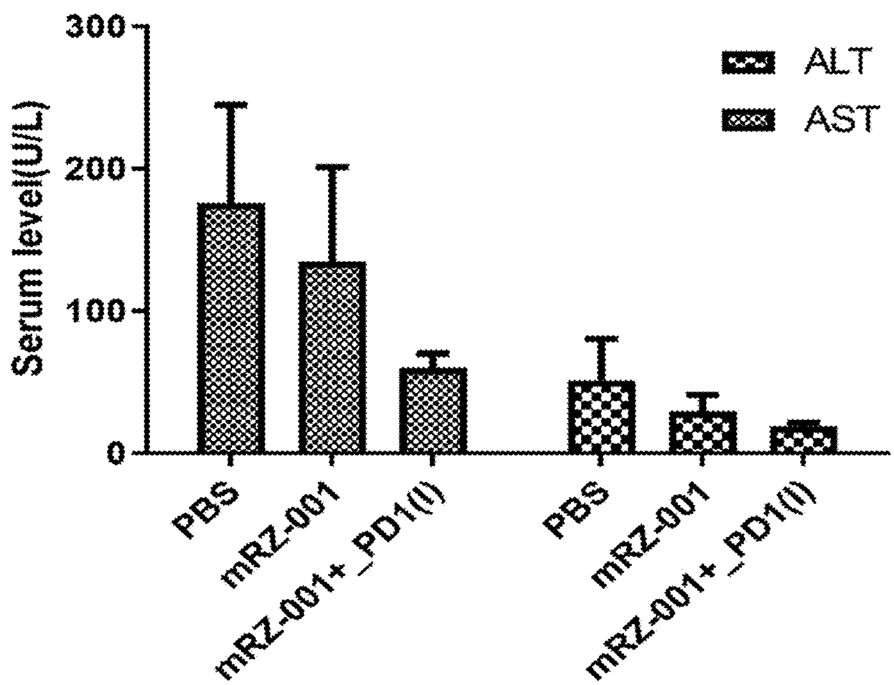
FIG. 23 illustrates a result of confirming serum ALT and AST levels of mRZ-001 and mRZ-001+-administered groups in an Orthotopic brain tumor syngeneic model.

Meanwhile, the mRZ-001+-administered group showed lower AST and ALT levels than the control group, indicating that the treated samples had significantly low toxicity in vivo (FIG. 23).

Figure 24:
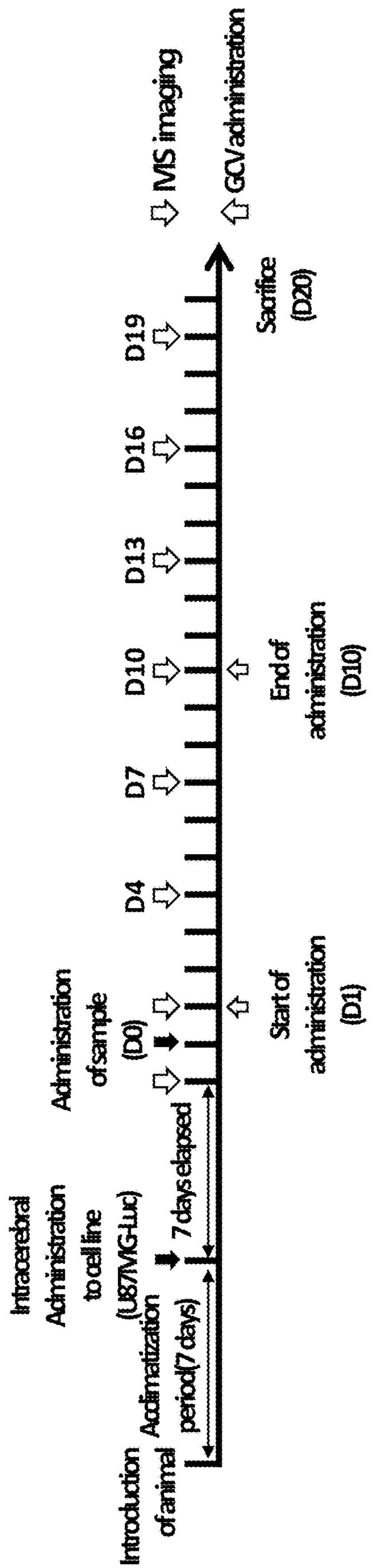
FIG. 24 is a schematic diagram of an experiment for confirming an effect of RZ-001+ in a xenograft orthotopic brain tumor model.

7-3. Confirmation of Effect of RZ-001+ in Xenograft Orthotopic Brain Tumor Model Following Embodiment 32, the anticancer effect of RZ-001+ was confirmed in an animal model transplanted with human-derived brain tumor cells. Accordingly, a 5-week-old male BALB/C nude mouse was transplanted in the same manner as in Embodiment 7-32 using human-derived brain tumor cells U87MG-Luci stably expressing Luciferase to prepare a xenograft orthotopic mouse brain tumor model. After 7 days, tumor growth was measured through IVIS imaging, group separation was performed, and drug administration was performed for each group (FIG. 24).

Administration of the drug was performed according to the following dosage and usage:

For RZ-001 and RZ-001+ AT, 1×10 10 VP/Head was administered directly into the tumor once;

GCV was administered at 50 mg/kg once daily from the next day after the end of virus administration, a total of 10 times.

Figure 25:
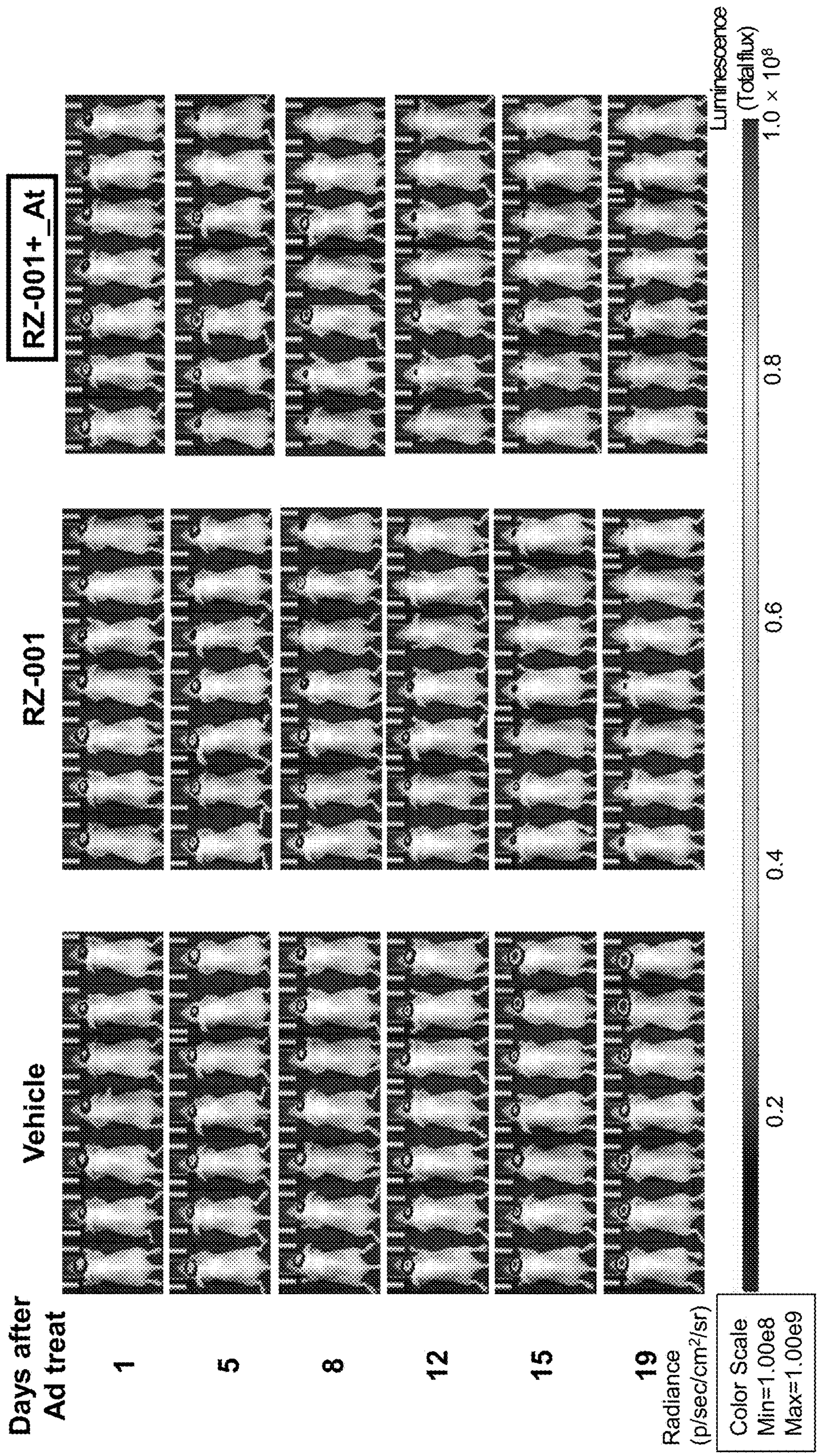
FIG. 25 shows an IVIS image according to an experimental progress of mice administered with RZ-001 or RZ-001+ to a xenograft orthotopic brain tumor model.
Figure 26:
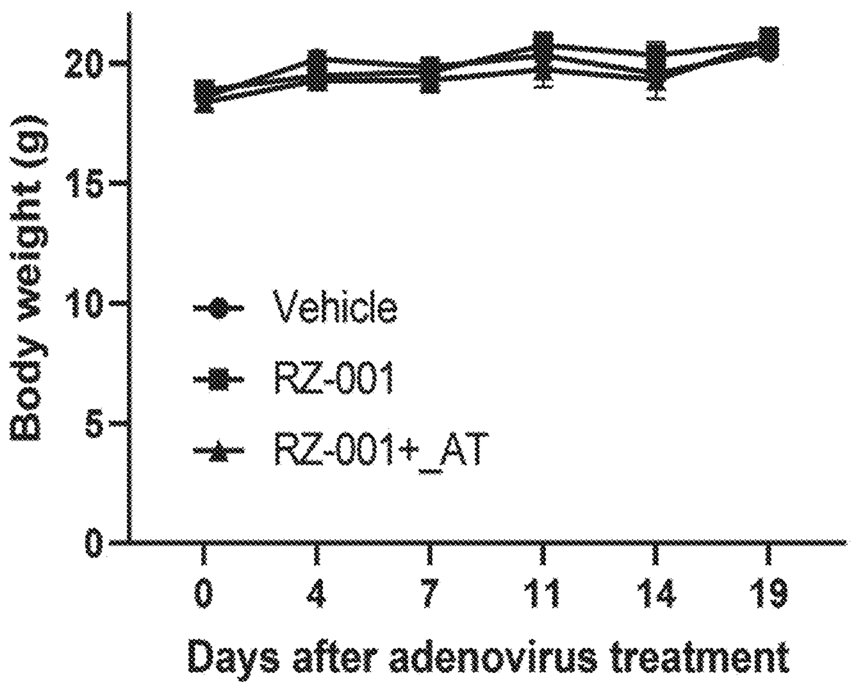
FIG. 26 illustrates a result of confirming changes in body weight according to an experimental progress of mice administered with RZ-001 or RZ-001+ to a xenograft xrthotopic brain tumor model.
Figure 27:
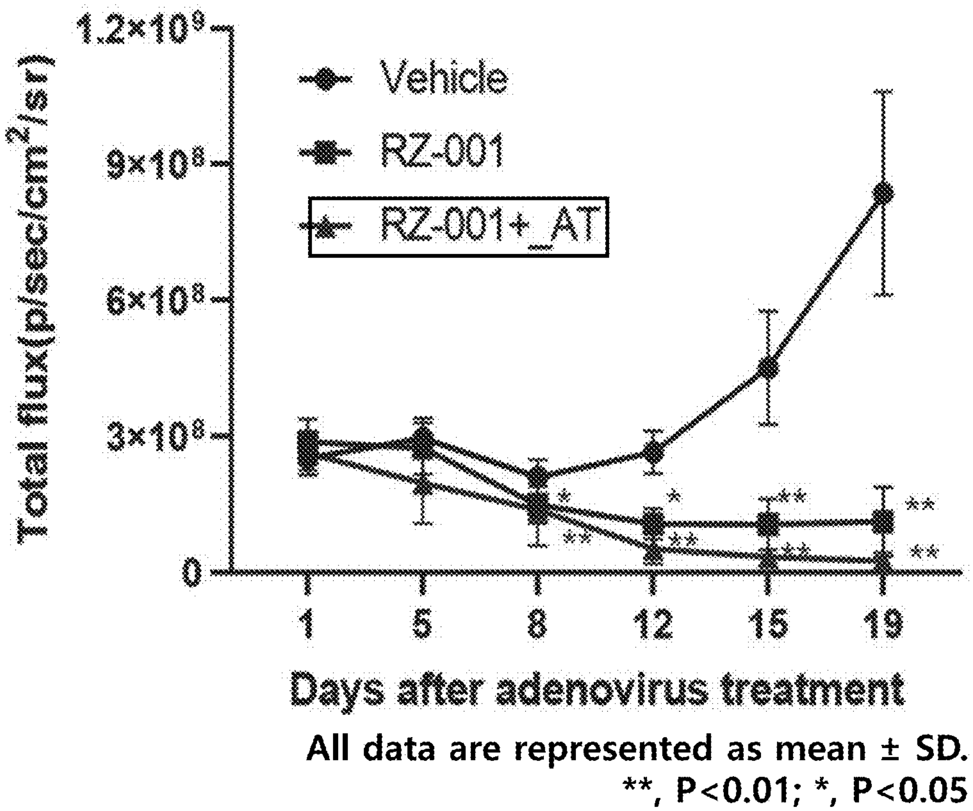
FIG. 27 illustrates a result confirming an anticancer effect of RZ-001 or RZ-001+ in a xenograft orthotopic brain tumor model.

After virus administration, IVIS imaging was performed at 3-day intervals to track the growth of luciferase-expressing tumor cells, and after 19 days of virus administration, finally, the mice were sacrificed and autopsied on the next day (Day 20) after IVIS imaging (FIG. 25). As the mice in each drug-administered group maintained a steady body weight during the experimental period, it could be seen that there was no or very low toxicity of RZ-001+(FIG. 26). Meanwhile, both RZ-001 and RZ-001+ were excellent in an anticancer effect, and in particular, it was confirmed that the anticancer activity of RZ-001+ At was superior to that of RZ-001, and thus, it can be seen that RZ-001+ has excellent an anticancer effect even in brain tumors (FIG. 27).

As described above, although the embodiments have been described by the restricted drawings, various modifications and variations can be applied on the basis of the embodiments by those skilled in the art. For example, even if the described techniques are performed in a different order from the described method, and/or components such as a system, a structure, a device, a circuit, and the like described above are coupled or combined in a different form from the described method, or replaced or substituted by other components or equivalents, an appropriate result can be achieved.

Therefore, other implementations, other embodiments, and equivalents to the appended claims fall within the scope of the claims to be described below.

INDUSTRIAL APPLICABILITY

According to the present disclosure, a trans-splicing ribozyme targeting a cancer-specific gene expresses a cancer therapeutic gene and an immune checkpoint inhibitor at the same time to exhibit a synergistic effect on anticancer efficacy, and thus it is expected to be useful for cancer treatment.

The invention claimed is:

1. A trans-splicing ribozyme targeting telomerase reverse transcriptase (TERT) mRNA, wherein the ribozyme has a structure of 5'-TERT mRNA targeting trans-splicing ribozyme–a cancer therapeutic gene–a self-cleaving peptide gene–an immune checkpoint inhibitor gene-3', and the cancer therapeutic genes is distinguished from the immune checkpoint inhibitor gene.

2. The trans-splicing ribozyme of claim 1, wherein the cancer therapeutic genes is selected from the group consisting of an agent-sensitizing gene, a proapoptotic gene, a cytostatic gene, a cytotoxic gene, a tumor suppressor gene, an antigenic gene, a cytokine gene, and an anti-angiogenic gene.

3. The trans-splicing ribozyme of claim 2, wherein the agent-sensitizing gene is Herpes Simplex Virus thymidine kinase (HSVtk).

4. The trans-splicing ribozyme of claim 1, wherein the immune checkpoint inhibitor gene is an inhibitor of CTLA-4, PD-1, PD-L1, PD-L2, LAG-3, BTLA, B7H3, B7H4, TIM3, KIR, TIG1T, CD47, VISTA, or A2aR.

5. The trans-splicing ribozyme of claim 1, further comprising:

at least one copy of a sequence complementary to part or all of microRNA-122a (miR-122a) at a 3'-terminal.

6. The trans-splicing ribozyme of claim 1, wherein the self-cleaving peptide is P2A.

7. An expression vector comprising the trans-splicing ribozyme of claim 1, capable of expressing the trans-splicing ribozyme of claim 1.

8. The expression vector of claim 7, further comprising: a promoter operably linked to the ribozyme.

9. A cell transformed with the expression vector of claim 7.

10. A pharmaceutical composition for treatment of cancer comprising the expression vector of claim 7 as an active ingredient.

11. The pharmaceutical composition of claim 10, wherein the pharmaceutical composition is administered orally or in a form of injection through an intravenous, intraarterial, cancerous tissue, or subcutaneous route.

12. The pharmaceutical composition of claim 10, wherein the cancer is at least one selected from the group consisting of liver cancer, glioblastoma, biliary tract cancer, lung cancer, pancreatic cancer, melanoma, bone cancer, breast cancer, colon cancer, stomach cancer, prostate cancer, leukemia, uterine cancer, ovarian cancer, lymphoma, and brain cancer.

13. The pharmaceutical composition of claim 10, wherein the cancer is immune checkpoint inhibitor resistant cancer.

14. A method for treatment of cancer comprising administering the composition of claim 10 to a non-human subject.

15. A pharmaceutical composition for treatment of cancer comprising the trans-splicing ribozyme of claim 1 as an active ingredient.

* * * * *